(12) United States Patent
Liao et al.

(10) Patent No.: US 11,230,544 B1
(45) Date of Patent: Jan. 25, 2022

(54) SUBSTITUTED 1,3,4-THIADIAZOLES AS GLS1 INHIBITORS

(71) Applicant: MEDSHINE DISCOVERY INC., Jiangsu (CN)

(72) Inventors: Yonggang Liao, Shanghai (CN); Jun Lin, Shanghai (CN); Chaonan Liu, Shanghai (CN); Changqing Wei, Shanghai (CN); Wenyuan Qian, Shanghai (CN); Chen Zhang, Shanghai (CN); Zhen Gong, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 0 days.

(21) Appl. No.: 17/284,806

(22) PCT Filed: Oct. 15, 2019

(86) PCT No.: PCT/CN2019/111232
§ 371 (c)(1),
(2) Date: Apr. 13, 2021

(87) PCT Pub. No.: WO2020/078350
PCT Pub. Date: Apr. 23, 2020

(30) Foreign Application Priority Data

Oct. 16, 2018 (CN) .......................... 201811202713.0

(51) Int. Cl.
| | | |
|---|---|---|
| *C07D 285/135* | (2006.01) | |
| *C07D 417/14* | (2006.01) | |
| *C07D 417/12* | (2006.01) | |
| *A61P 35/00* | (2006.01) | |
| *C07D 487/04* | (2006.01) | |

(52) U.S. Cl.
CPC ............ *C07D 417/14* (2013.01); *A61P 35/00* (2018.01); *C07D 417/12* (2013.01); *C07D 487/04* (2013.01)

(58) Field of Classification Search
CPC ................................................ C07D 285/135
USPC ......................................................... 548/139
See application file for complete search history.

(56) References Cited

U.S. PATENT DOCUMENTS

| 2013/0157998 A1 | 6/2013 | Li et al. |
| 2017/0333429 A1 | 11/2017 | Perkins et al. |

FOREIGN PATENT DOCUMENTS

| CN | 106890184 A | 6/2017 |
| CN | 108349965 A | 7/2018 |
| WO | 2015181539 A1 | 12/2015 |
| WO | 2017004359 A1 | 1/2017 |
| WO | 2017093299 A1 | 6/2017 |
| WO | 2017093300 A1 | 6/2017 |
| WO | 2017093301 A1 | 6/2017 |

OTHER PUBLICATIONS

Jan. 19, 2020 International Search Report issued in International Patent Application No. PCT/CN2019/111232.
Jan. 19, 2020 International Written Opinion issued in International Patent Application No. PCT/CN2019/111232.
Jul. 6, 2021 the First Canadian Office Action issued in Canadian application No. 3116440.
Oct. 5, 2021 the EESR issued in European application No. 19874268.6.
Oct. 12, 2021 the First Office Action issued in Japanese application No. 2021-521183.
Oct. 5, 2021 the First Office Action issued in Korean application No. 10-2021-7014579.
Oct. 11, 2021 the First Office Action issued in Australian application No. 2019363115.

*Primary Examiner* — Douglas M Willis
(74) *Attorney, Agent, or Firm* — Liangang Ye; Houston Beshining Law Office PLLC

(57) ABSTRACT

Disclosed is to a thiadiazole derivative and the uses thereof in preparing a drug for treating GLS1-associated diseases. Specifically disclosed is a derivative compound of formula (I), a tautomer thereof or a pharmaceutically acceptable composition thereof.

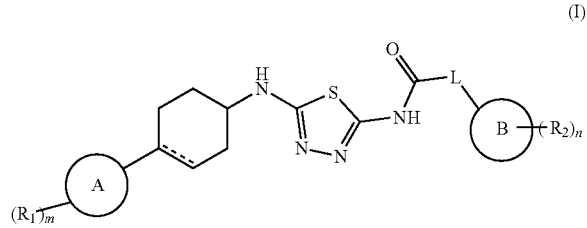

21 Claims, 1 Drawing Sheet

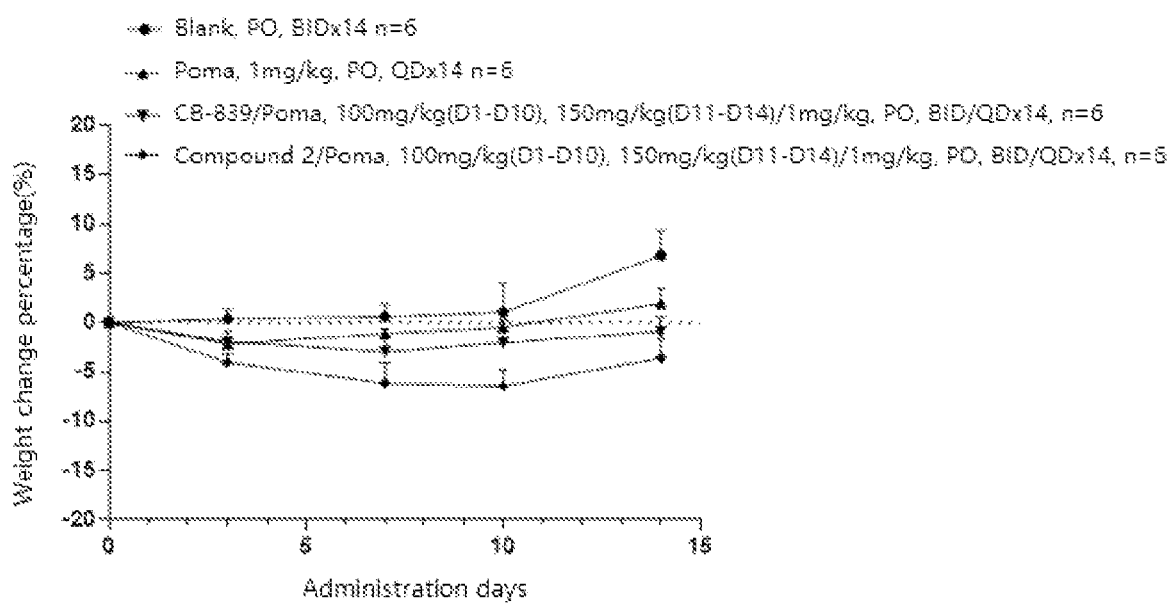

SUBSTITUTED 1,3,4-THIADIAZOLES AS GLS1 INHIBITORS

The present application is a National Stage of International Application No. PCT/CN2019/111232, filed on Oct. 15, 2019 which claims priority of the Chinese Patent Application No. CN 201811202713.0, filed on Oct. 16, 2018, the contents of which are incorporated herein by reference in their entireties.

TECHNICAL FIELD

The present disclosure relates to a thiadiazole derivative and the uses thereof in the manufacture of a drug for treating GLS1-associated diseases. Specifically, the present disclosure relates to a derivative compound of formula (I), a tautomer thereof or a pharmaceutically acceptable compound thereof.

BACKGROUND

Glutamine is the most abundant amino acid in the human body, and is a non-essential amino acid. Some glutamines are taken up from the circulation by the amidation of glutamate and ammonia derived from purine metabolism, and other glutamines are produced by the transamination of α-ketoglutarate derived from glucose and subsequent amidation. Glutaminase (GLS) can promote the decomposition of glutamine into glutamate and ammonium ions, and then the glutamate is converted to α-KG (α-ketoglutarate) by a glutamate dehydrogenase, and then the α-KG enters the TCA cycle (tricarboxylic acid cycle) to provide energy and a source of macromolecular materials. More importantly, the carbon source produced by glutamine metabolism supports the synthesis of OAA (oxaloacetic acid), acetyl coenzyme A and citric acid, and lipogenesis; at the same time, the nitrogen source produced by glutamine metabolism supports the synthesis of purines, pyrimidines, DNA, NADPH (nicotinamide adenine dinucleotide phosphate) and GSH (glutathione) to maintain redox homeostasis. Glutamine acts as a precursor for the synthesis of many amino acids, proteins, nucleotides and other biologically important molecules.

Glutamine plays a key role in cell growth and proliferation. It is well known that cancer cells use glucose to produce ATP (adenosine triphosphate) through aerobic glycolysis in a dissipative way; at the same time, in order to meet rapid proliferation, cancer cells must use another energy source glutamine to produce ATP through oxidative phosphorylation. Due to the continuous loss of citrate from the TCA cycle in proliferative cells, especially cancer cells, it is necessary to replenish a large amount of TCA intermediates to increase glutamine consumption for anabolic needs. Compared with normal tissues, glutamine has increased demand and accelerated consumption in most cancer cells, and the GLS activity in cancer cells is much higher than that in normal cells. Elevated glutamine metabolism not only provides energy and substrates for the growth and proliferation of cancer cells, but also makes glutamine an effective candidate in cancer treatment.

Restriction on glutamine metabolism can effectively inhibit the growth of cancer cells. As the first key enzyme in glutamine metabolism, specific inhibitors for GLS can induce cell death in cancer cells. There are two reported glutaminase inhibitors, one is CB-839 developed by Calithera Biosciences and the other is a compound called 968, which is developed by Cornell University and is undergoing clinical trials.

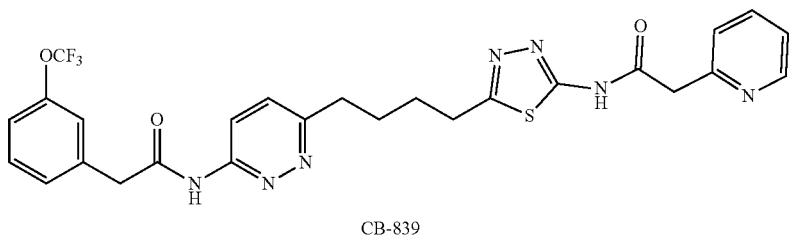 [SMILES: O=C(Cc1cccc(OC(F)(F)F)c1)Nc1ccc(CCCCc2nnc(NC(=O)Cc3ccccn3)s2)nn1]

CB-839

At present, there is still a need to develop new glutaminase inhibitors for the treatment of diseases related to cell proliferation.

CONTENT OF THE PRESENT INVENTION

The present disclosure provides a compound of formula (I), an isomer thereof or a pharmaceutically acceptable salt thereof,

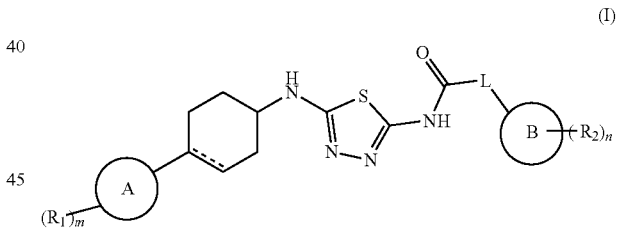

wherein

is selected from a single bond and a double bond;
$R_1$ is independently selected from H, F, Cl, Br, I, OH, $NH_2$, CN, COOH, $C_{1-6}$ alkyl and $C_{1-6}$ heteroalkyl, wherein the $C_{1-6}$ alkyl and $C_{1-6}$ heteroalkyl are optionally substituted with 1, 2, or 3 $R_a$;
$R_2$ is independently selected from H, F, Cl, Br, I, OH, $NH_2$, CN, COOH, $C_{1-6}$ alkyl and $C_{1-6}$ heteroalkyl, wherein the $C_{1-6}$ alkyl and $C_{1-6}$ heteroalkyl are optionally substituted with 1, 2, or 3 $R_b$;
L is selected form —$C(R_c)(R_d)$—;
ring A is selected from 5- to 10-membered heteroaryl;
ring B is selected from phenyl and 5- to 6-membered heteroaryl;

m is selected from 1, 2 and 3;
n is selected from 1, 2 and 3;
$R_a$ and $R_b$ are each independently selected from F, Cl, Br, I, OH, $NH_2$, CN and COOH;
$R_c$ and $R_d$ are each independently selected from H, F, Cl, Br, I, OH, $NH_2$, CN, COOH, $C_{1-6}$ alkyl and $C_{1-6}$ heteroalkyl, wherein the $C_{1-3}$ alkyl and $C_{1-3}$ alkoxy are optionally substituted with 1, 2, or 3 R;
R is selected from F, Cl, Br, I, OH, $NH_2$, CN, COOH and $CH_3$;
the $C_{1-6}$ heteroalkyl, 5- to 6-membered heteroaryl and 5- to 10-membered heteroaryl each independently comprise 1, 2, 3 or 4 heteroatoms or heteroatomic groups independently selected from —NH—, —O—, —S— and N.

In some embodiments of the present disclosure, the above-mentioned $R_1$ is independently selected from H, F, Cl, Br, I, OH, $NH_2$, CN, COOH, $C_{1-6}$ alkyl or $C_{1-6}$ heteroalkyl, wherein the $C_{1-6}$ alkyl and $C_{1-6}$ heteroalkyl are optionally substituted with 1, 2, or 3 $R_a$.

In some embodiments of the present disclosure, the above-mentioned $R_2$ is independently selected from H, F, Cl, Br, I, OH, $NH_2$, CN, COOH, $C_{1-6}$ alkyl or $C_{1-6}$ heteroalkyl, wherein the $C_{1-6}$ alkyl or $C_{1-6}$ heteroalkyl is optionally substituted with 1, 2, or 3 $R_b$.

In some embodiments of the present disclosure, the above-mentioned $R_1$ is independently selected from H, F, Cl, Br, I, OH, $NH_2$, CN, COOH, $C_{1-3}$ alkyl and $C_{1-3}$ alkoxy, wherein the $C_{1-3}$ alkyl and $C_{1-3}$ alkoxy are optionally substituted with 1, 2, or 3 $R_a$, and other variables are as defined in the present disclosure.

In some embodiments of the present disclosure, the above-mentioned $R_1$ is selected from H, F, Cl, Br, I, OH, $NH_2$, CN, COOH, $C_{1-3}$ alkyl and $C_{1-3}$ alkoxy, wherein the $C_{1-3}$ alkyl and $C_{1-3}$ alkoxy are optionally substituted with 1, 2, or 3 $R_a$, and other variables are as defined in the present disclosure.

In some embodiments of the present disclosure, the above-mentioned $R_1$ is independently selected from H, F, Cl, Br, I, OH, $NH_2$, CN, COOH, $CH_3$, $CH_2CH_3$ and

wherein the $CH_3$, $CH_2CH_3$ and

are optionally substituted with 1, 2, or 3 $R_a$, and other variables are as defined in the present disclosure.

In some embodiments of the present disclosure, the above-mentioned $R_1$ is independently selected from H, F, Cl, Br, I, OH, $NH_2$, CN, COOH, $CH_3$, $CH_2F$, $CHF_2$, $CF_3$, $CH_2CH_3$,

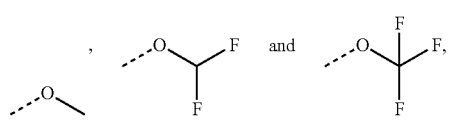

and other variables are as defined in the present disclosure.

In some embodiments of the present disclosure, the above-mentioned $R_2$ is independently selected from H, F, Cl, Br, I, OH, $NH_2$, CN, COOH, $C_{1-3}$ alkyl and $C_{1-3}$ alkoxy, wherein the $C_{1-3}$ alkyl and $C_{1-3}$ alkoxy are optionally substituted with 1, 2, or 3 $R_b$, and other variables are as defined in the present disclosure.

In some embodiments of the present disclosure, the above-mentioned $R_2$ is independently selected from H, F, Cl, Br, I, OH, $NH_2$, CN, COOH, $CH_3$, $CH_2CH_3$ and

wherein the $CH_3$, $CH_2CH_3$ and

are optionally substituted with 1, 2, or 3 $R_b$, and other variables are as defined in the present disclosure.

In some embodiments of the present disclosure, the above-mentioned $R_2$ is independently selected from H, F, Cl, Br, I, OH, $NH_2$, CN, COOH, $CH_3$, $CH_2F$, $CHF_2$, $CF_3$, $CH_2CH_3$,

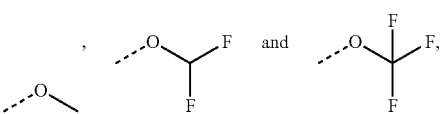

and other variables are as defined in the present disclosure.

In some embodiments of the present disclosure, the above-mentioned $R_c$ and $R_d$ are each independently selected from H, F, Cl, Br, I, OH, $NH_2$, CN, COOH, $C_{1-3}$ alkyl and $C_{1-3}$ alkoxy, wherein the $C_{1-3}$ alkyl and $C_{1-3}$ alkoxy are optionally substituted with 1, 2, or 3 R, and other variables are as defined in the present disclosure.

In some embodiments of the present disclosure, the above-mentioned $R_c$ and $R_d$ are each independently selected from H, F, Cl, Br, I, OH, $NH_2$, CN, COOH, $CH_3$, $CF_3$, $CH_2CH_3$ and

and other variables are as defined in the present disclosure.

In some embodiments of the present disclosure, the above-mentioned L is selected from —$CH_2$— and

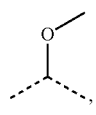

and other variables are as defined in the present disclosure.

In some embodiments of the present disclosure, the above-mentioned L is selected from

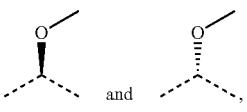

and other variables are as defined in the present disclosure.

In some embodiments of the present disclosure, the above-mentioned ring A is selected from pyridinyl, pyridazinyl, pyrazinyl and 7H-pyrrolo[2,3-c]pyridazinyl, and other variables are as defined in the present disclosure.

In some embodiments of the present disclosure, the above-mentioned moiety

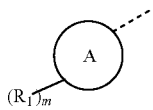

is selected from

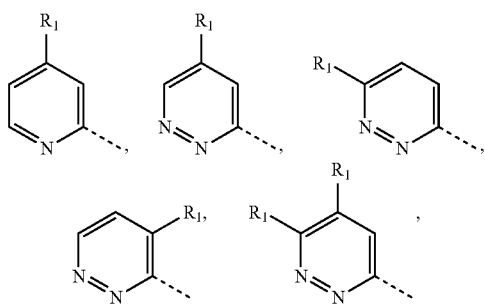

and other variables are as defined in the present disclosure.

In some embodiments of the present disclosure, the above-mentioned moiety

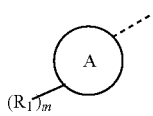

is selected from

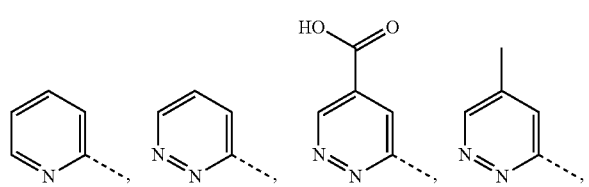

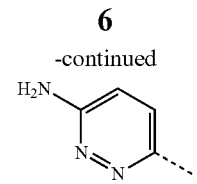

and

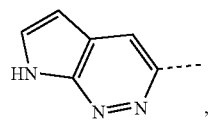

and other variables are as defined in the present disclosure.

In some embodiments of the present disclosure, the above-mentioned ring B is selected from phenyl, pyrazolyl and pyridyl, and other variables are as defined in the present disclosure.

In some embodiments of the present disclosure, the above-mentioned moiety

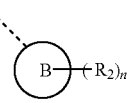

is selected from

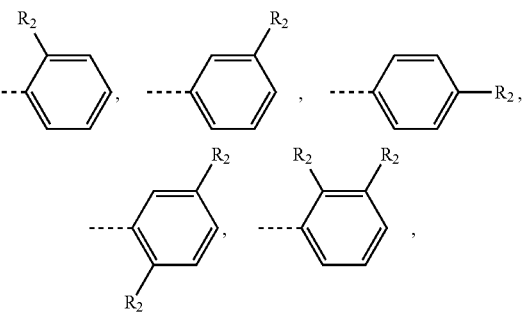

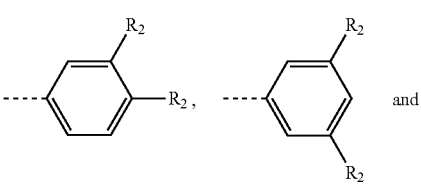

and

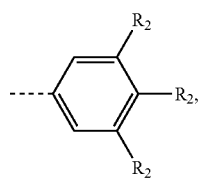

and other variables are as defined in the present disclosure.

In some embodiments of the present disclosure, the above-mentioned moiety

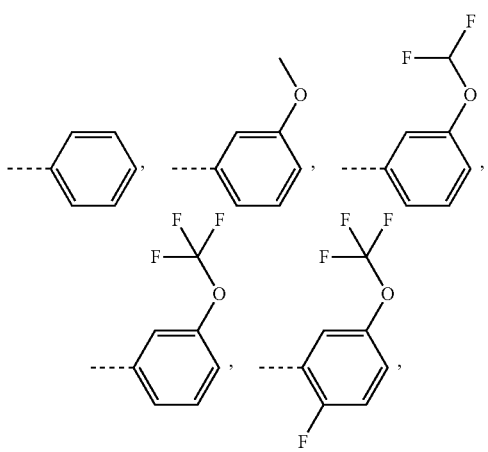

is selected from

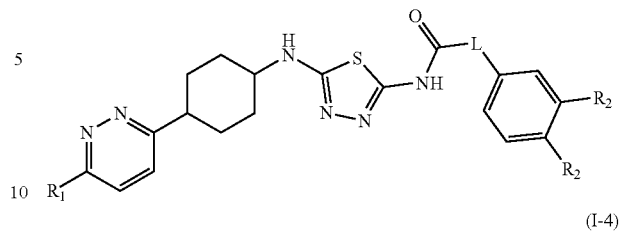

and

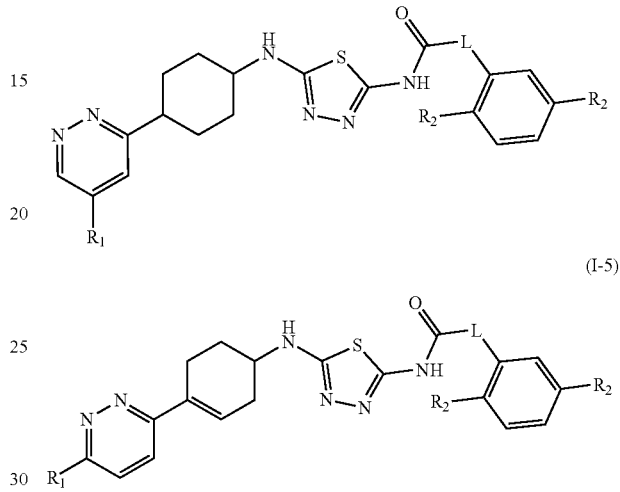

and other variables are as defined in the present disclosure.

Other embodiments of the present disclosure are generated by any combination of the above-mentioned variables.

In some embodiments of the present disclosure, the above-mentioned compound, isomer thereof or pharmaceutically acceptable salt thereof is selected from

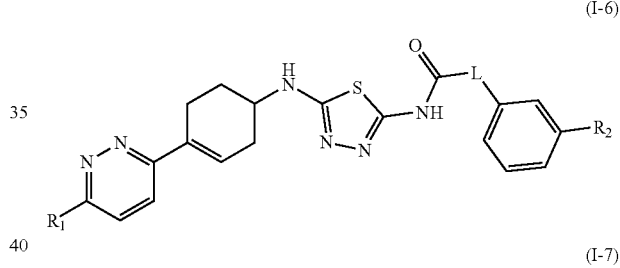

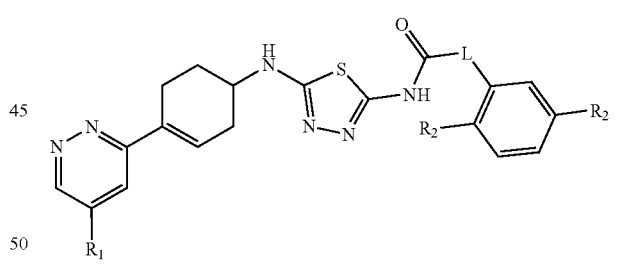

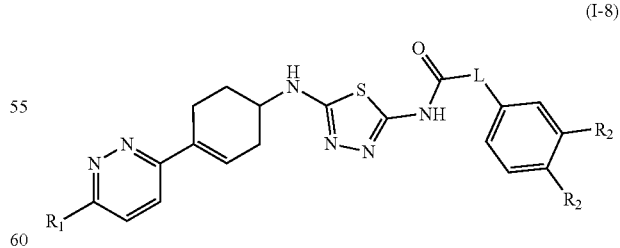

wherein $R_1$, $R_2$, L, m and n are as defined in the present disclosure.

In some embodiments of the present disclosure, the above-mentioned compound, isomer thereof or pharmaceutically acceptable salt thereof is selected from (I-1a)
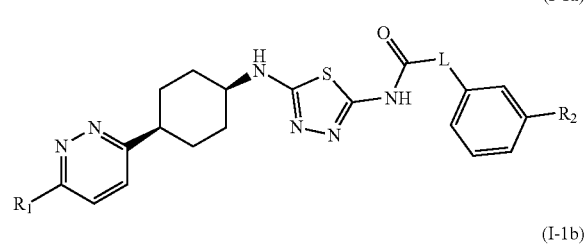
(I-1b)
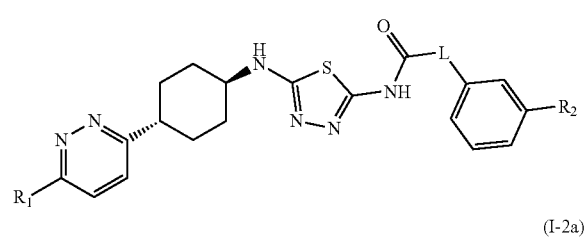
(I-2a)
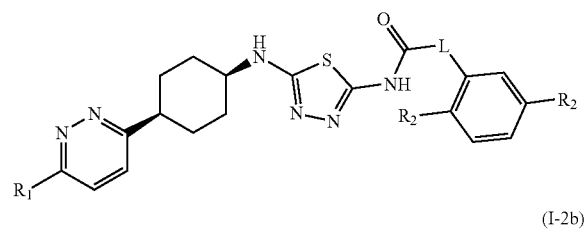
(I-2b)
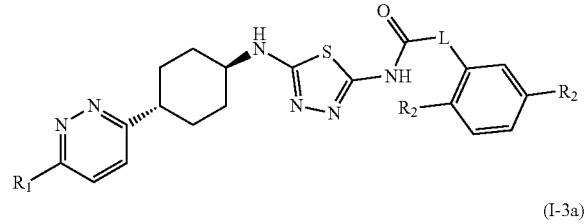
(I-3a)
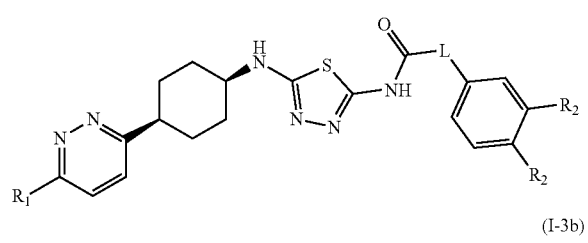
(I-3b)
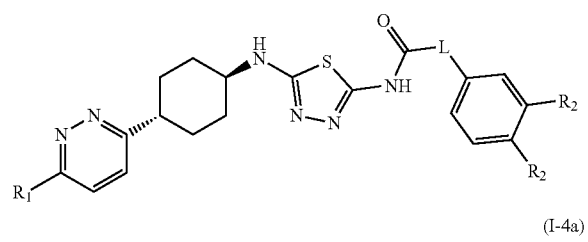
(I-4a)
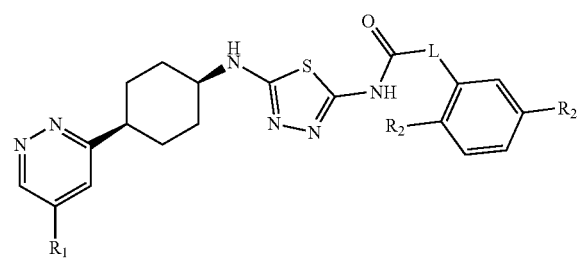
(I-4b)
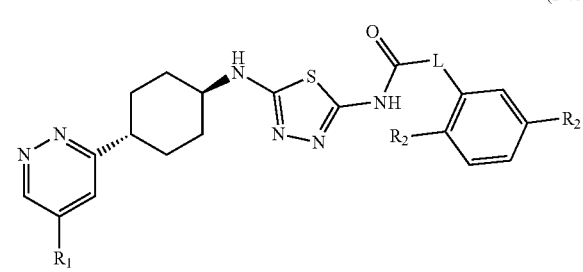
(I-5a)
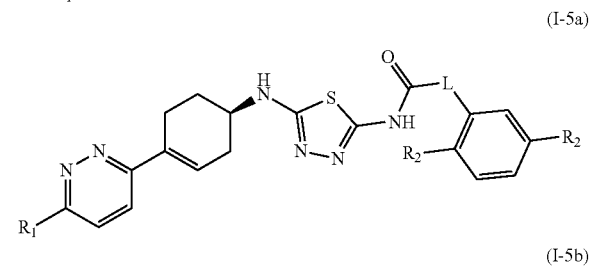
(I-5b)
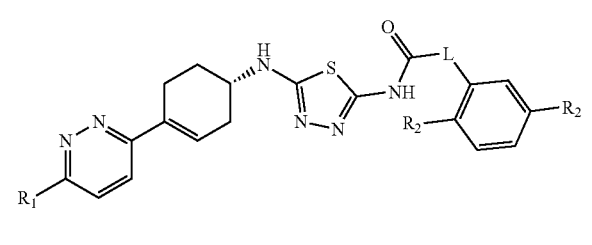
wherein
$R_1$, $R_2$, m and n are as defined in the present disclosure.
The present disclosure also provides a compound of the following formulas, an isomer thereof or a pharmaceutically acceptable salt thereof, wherein the compound is selected from
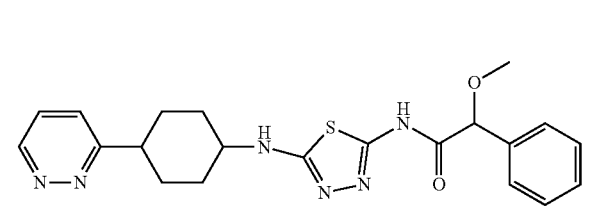
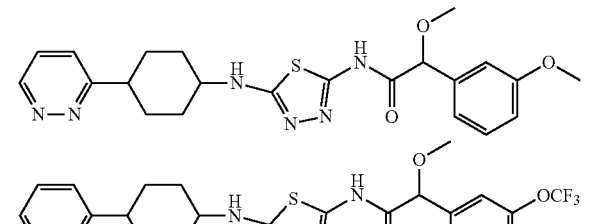
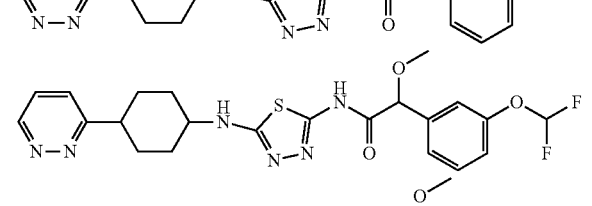
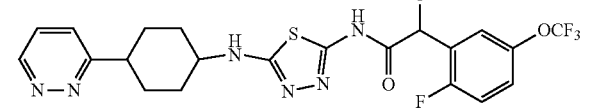

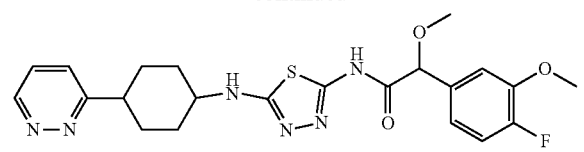
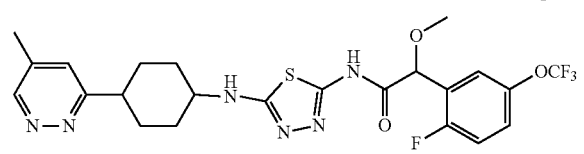
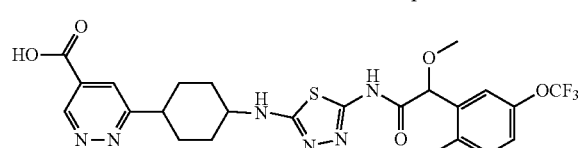
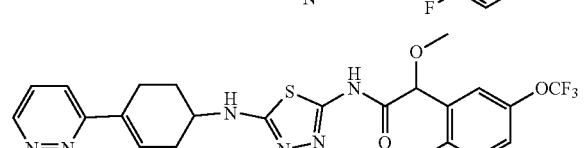
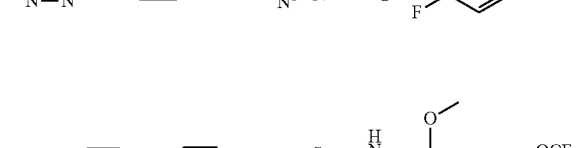
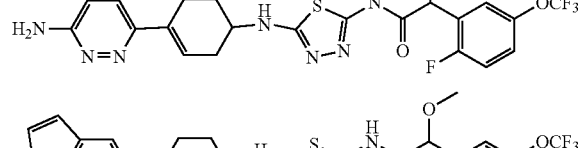
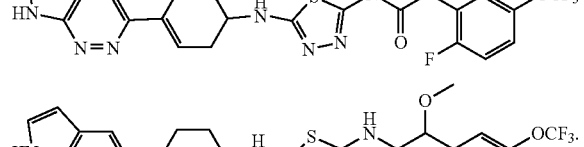
In some embodiments of the present disclosure, the above-mentioned compound is selected from
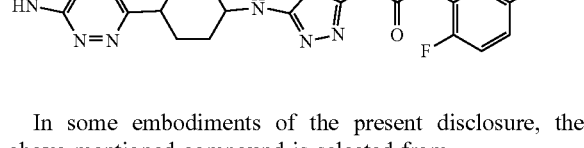
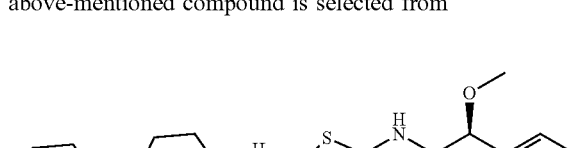
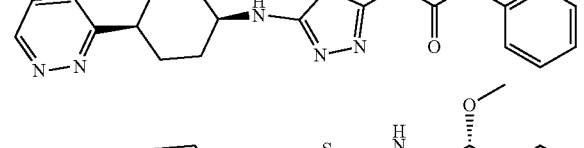
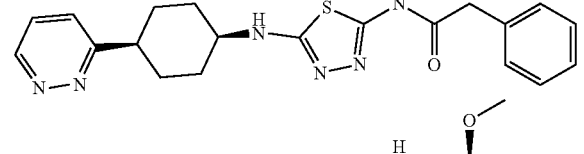
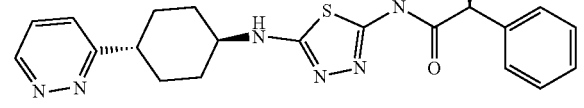
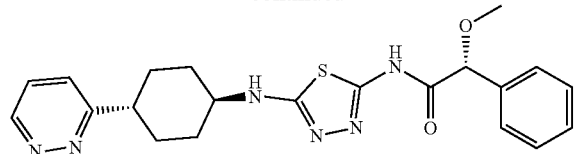
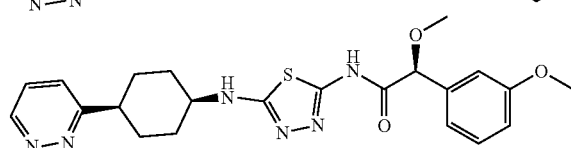
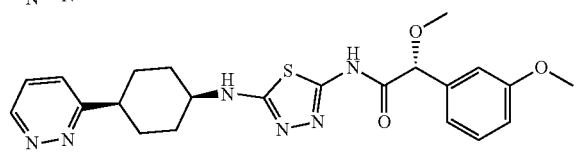
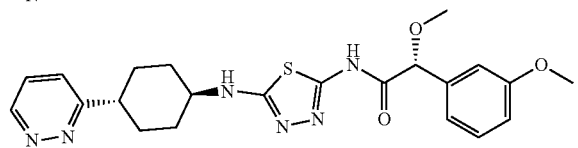
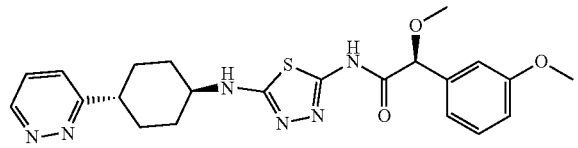
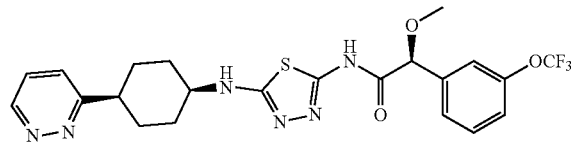
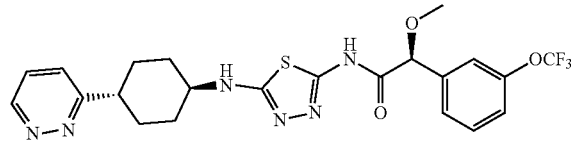
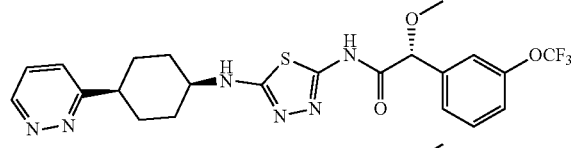
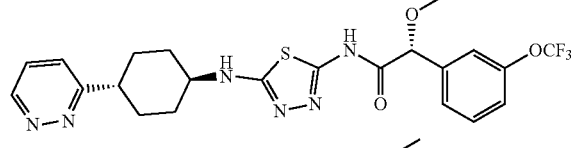
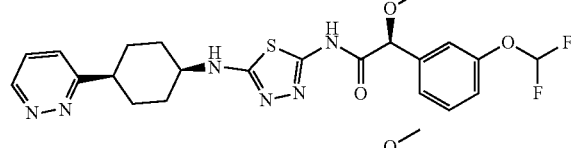
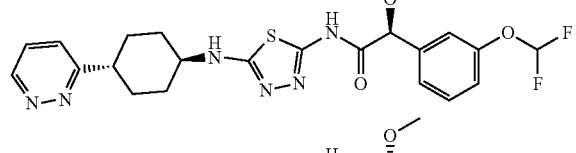
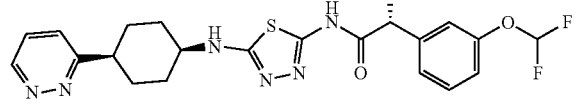

-continued
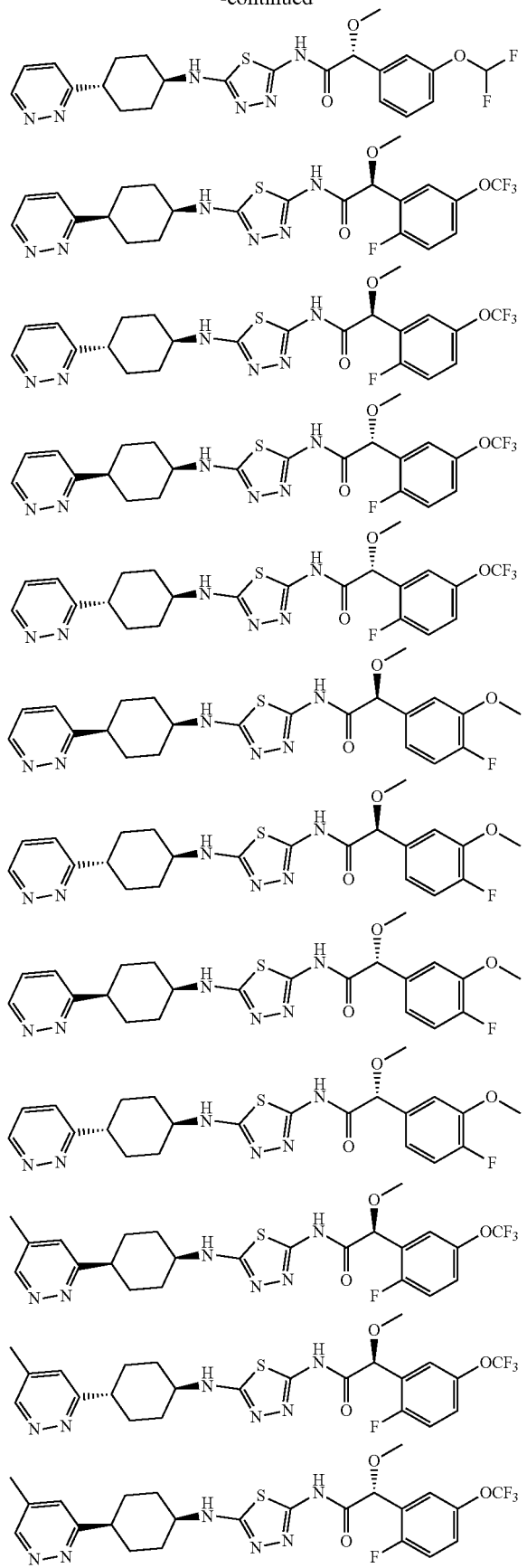
-continued
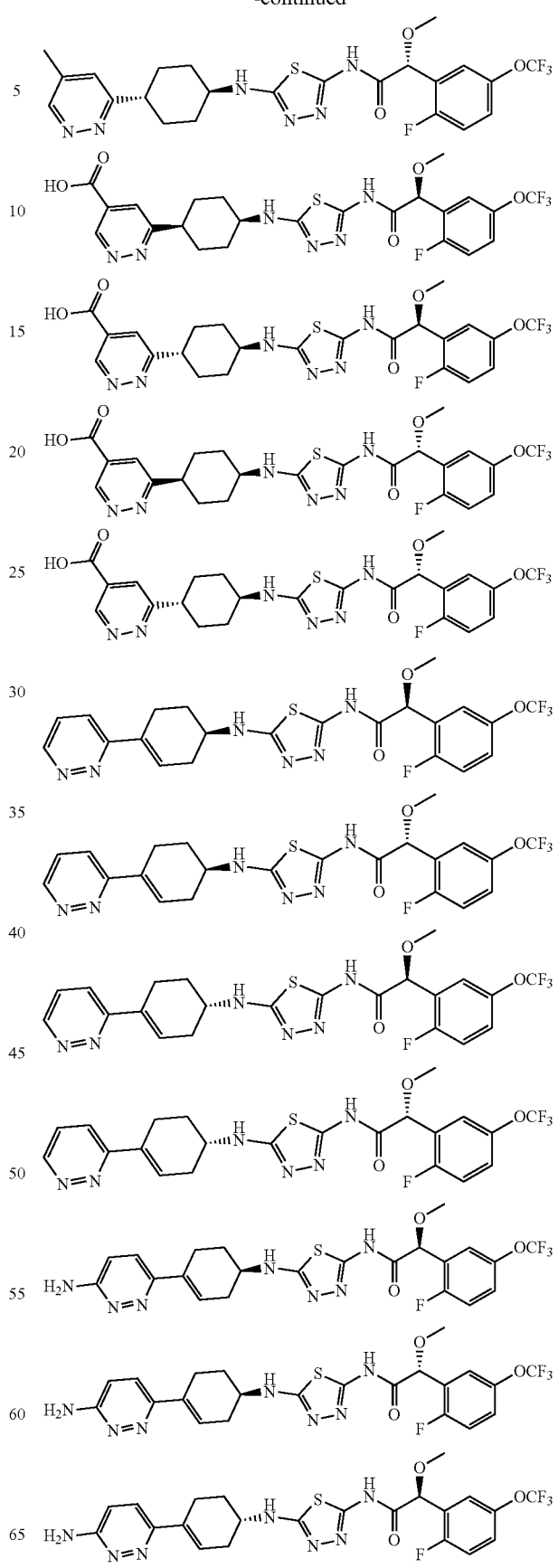

-continued

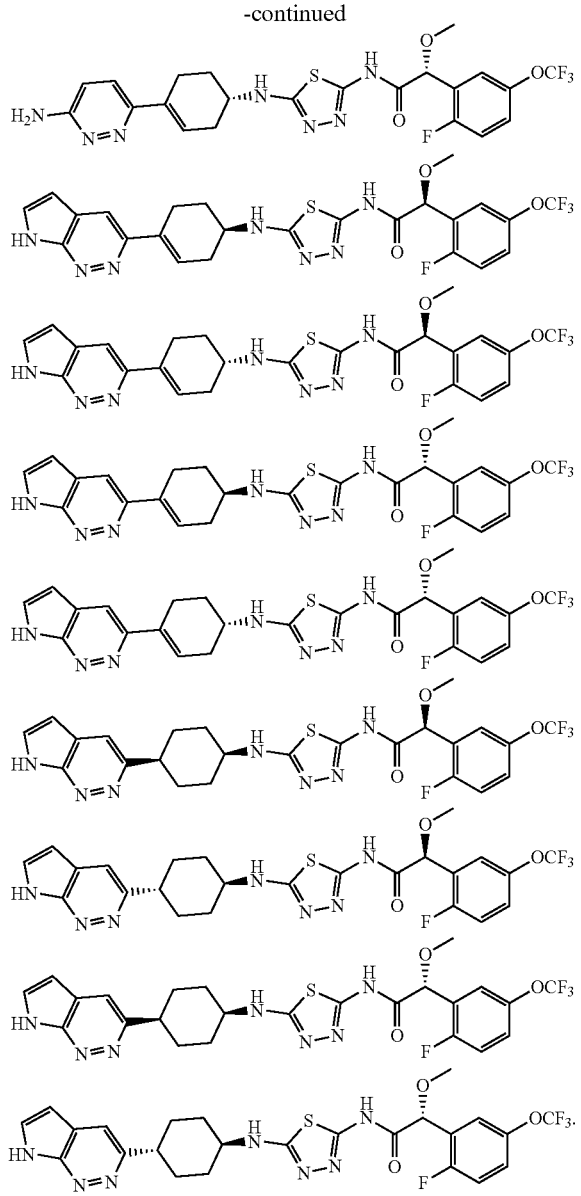

The present disclosure also provides use of the above-mentioned compound, isomer thereof or pharmaceutically acceptable salt thereof in the manufacture of a drug for treating GLS1-associated diseases.

Definition and Description

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to the corresponding commodity or an active ingredient thereof.

The term "pharmaceutically acceptable" as used herein refers to those compounds, materials, compositions and/or dosage forms, which are, within the scope of sound medical judgment, suitable for use in contact with human and animal tissues, without excessive toxicity, irritation, allergic reactions or other problems or complications, which is commensurate with a reasonable benefit/risk ratio.

The term "pharmaceutically acceptable salt" refers to a salt of the compound of the present disclosure, which is prepared from the compound having specific substituents found in the present disclosure with relatively non-toxic acids or bases. When compounds of the present disclosure contain relatively acidic functional groups, base addition salts can be obtained by contacting the neutral form of such compounds with a sufficient amount of base, either in pure solution or a suitable inert solvent. Pharmaceutically acceptable base addition salts include sodium, potassium, calcium, ammonium, organic amine or magnesium salts or similar salts. When compounds of the present disclosure contain relatively basic functional groups, acid addition salts can be obtained by contacting the neutral form of such compounds with a sufficient amount of acid, either in pure solution or a suitable inert solvent. Examples of pharmaceutically acceptable acid addition salts include salts of inorganic acids, which include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid and phosphorous acid; and salts of organic acids, which include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and also include salts of amino acids (such as arginine), and salts of organic acids such as glucuronic acid. Certain specific compounds of the present disclosure contain basic and acidic functional groups and thus can be converted to any base or acid addition salt.

The pharmaceutically acceptable salts of the present disclosure can be synthesized from a parent compound containing acid radicals or base radicals by conventional chemical methods. In general, the method for preparing such salts comprises: in water or an organic solvent or a mixture of both, reacting these compounds in free acid or base forms with a stoichiometric amount of a suitable base or acid to prepare the salts.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomers, (L)-isomers, and racemic mixtures and other mixtures thereof, such as enantiomerically or diastereomerically enriched mixtures, all of which fall within the scope of the present disclosure. Additional asymmetric carbon atoms may be present in a substituent such as an alkyl group. All these isomers and mixtures thereof are included in the scope of the present disclosure.

Unless otherwise stated, the term "enantiomer" or "optical isomers" refers to stereoisomers that are mirror images of each other.

Unless otherwise stated, the term "cis-trans isomer" or "geometric isomer" is caused by the fact that double bonds or single bonds of ring-forming carbon atoms cannot rotate freely.

Unless otherwise stated, the term "diastereomers" refers to stereoisomers in which molecules have two or more chiral centers and are not mirror images of each other.

Unless otherwise stated, "(D)" or "(+)" means dextrorotatory, "(L)" or "(−)" means levorotatory, and "(DL)" or "(±)" means racemic.

Unless otherwise stated, the wedge-shaped solid bond (◥) and the wedge-shaped dotted bond (◊) represent the absolute configuration of a stereoscopic center; the straight solid bond (◥) and the straight dotted bond (◊) represent the relative configuration of a stereoscopic center; the wavy line (∿) represents the wedge-shaped solid bond (◥) or the wedge-shaped dotted bond (◊); or the wavy line (∿) represents the straight solid bond (◥) and the straight dotted bond (◊).

The compounds of the present disclosure may exist in specific. Unless otherwise stated, the term "tautomer" or "tautomeric form" means that at room temperature, isomers with different functional groups are in dynamic equilibrium and can be quickly converted to each other. Where tautomerization is possible (such as in solution), a chemical equilibrium of tautomers can be achieved. For example, proton tautomers (also known as prototropic tautomers) include interconversion via migration of a proton, such as keto-enol isomerization and imine-enamine isomerization. Valence tautomers include some interconversions by recombination of some of the bond-forming electrons. A specific example of keto-enol tautomerization is the interconversion between two tautomers, pentane-2,4-dione and 4-hydroxypent-3-en-2-one.

Unless otherwise stated, the term "rich in one isomer", "isomer enriched", "rich in one enantiomer" or "enantiomerically enriched" refers to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomers and D and L isomers can be prepared using chiral synthesis or chiral reagents or other conventional techniques. If a particular enantiomer of a compound of the present disclosure is desired, it can be prepared by asymmetric synthesis or derivatization with a chiral auxiliary, wherein the resulting diastereomeric mixture is separated and the auxiliary groups are cleaved to provide pure desired enantiomers. Alternatively, where the molecule contains a basic functional group (such as an amino group) or an acidic functional group (such as a carboxyl group), diastereomeric salts can be formed with an appropriate optically active acid or base, followed by resolution of the diastereomers using conventional methods well known in the art, and subsequent recovery of the pure enantiomers. In addition, separation of enantiomers and diastereomers is frequently accomplished using chromatography, which uses chiral stationary phases, optionally in combination with chemical derivatization methods (e.g., formation of carbamates from amines). The compounds of the present disclosure may contain unnatural proportions of atomic isotopes at one or more of the atoms constituting the compound. For example, the compounds may be radiolabeled with radioactive isotopes, such as tritium ($^3$H), iodine-125 ($^{125}$I) or C-14 ($^{14}$C). For another example, the hydrogen can be substituted by heavy hydrogen to form deuterated drugs. The bond formed by deuterium and carbon is stronger than the bond formed by ordinary hydrogen and carbon. Compared with undeuterated drugs, deuterated drugs have reduced toxic side effects, increased drug stability, enhanced efficacy, prolonged biological half-life of drugs and other advantages. All isotopic variations of the compounds of the present disclosure, whether radioactive or not, are intended to be encompassed within the scope of the present disclosure.

"Optional" or "optionally" means that the subsequently described event or circumstance may, but not necessarily occur, and that the description includes instances where said event or circumstance occurs and instances where said event or circumstance does not occur.

The term "substituted" means that any one or more hydrogen atoms on the designated atom are substituted by a substituent, which may include heavy hydrogen and hydrogen variants, provided that the valence state of the designated atom is normal, and the substituted compound is stable. Where the substituent is oxygen (i.e., =O), it means that two hydrogen atoms are substituted. Oxygen substitution does not occur on aromatic groups. The term "optionally substituted" means that it may or may not be substituted. Unless otherwise specified, the type and number of substituents may be arbitrary on the basis that they can be achieved in chemistry.

Where any variable (such as R) appears more than once in the composition or structure of a compound, its definition in each case is independent. Thus, for example, if a group is substituted with 0-2 R, the group can optionally be substituted with up to two R, and R in each case has independent options. In addition, combinations of substituents and/or variants thereof are permissible only if such combinations result in stable compounds.

When the number of a linking group is 0, such as —(CRR)$_0$—, it means that the linking group is a single bond.

When one of the variables is selected from a single bond, it means that the two groups to which it is connected are directly connected. For example, when L represents a single bond in A-L-Z, it means that the structure is actually A-Z.

When a substituent is vacant, it means that the substituent does not exist. For example, when X is vacant in A-X, it means that the structure is actually A. When the substituents listed do not indicate through which atom they are connected to the substituted group, such substituents can be bonded through any of the atoms thereof, for example, pyridyl as a substituent can be attached to the substituted group via any carbon atom on the pyridine ring. When the linking group listed does not indicate the linking direction thereof, the linking direction is arbitrary, for example, the linking group L is -M-W— in

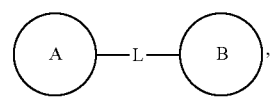

at this situation, -M-W— can connect ring A and ring B in the same direction as the reading order from left to right to form

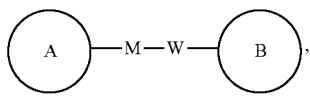

and can also connect ring A and ring B in the opposite direction as the reading order from left to right to form

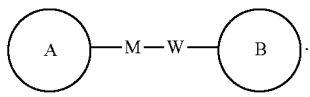

Combinations of the linking groups, substituents, and/or variants thereof are permissible only if such combinations result in stable compounds.

Unless otherwise specified, the term "hetero" means heteroatoms or heteroatomic groups (i.e., atomic groups containing heteroatoms), including atoms other than carbon (C) and hydrogen (H) and atomic groups containing these heteroatoms, such as oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, the term "hydrocarbyl" or its subordinate concept (such as alkyl, alkenyl, alkynyl and aryl) by itself or as part of another substituent means linear, branched or cyclic hydrocarbon atomic groups or combinations thereof, which may be fully saturated (such as alkyl), mono-unsaturated or poly-unsaturated (such as alkenyl, alkynyl and aryl), may be mono-substituted or poly-substituted, may be monovalent (such as methyl), divalent (such as methylene) or polyvalent (such as methine), and may include divalent or polyvalent atomic groups, with a specified number of carbon atoms (for example, $C_1$-$C_{12}$ means 1 to 12 carbons; $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). "Hydrocarbyl" includes, but is not limited to, aliphatic hydrocarbyl and aromatic hydrocarbyl, wherein the aliphatic hydrocarbyl includes a chain structure and a cyclic structure, specifically including but not limited to alkyl, alkenyl and alkynyl, and the aromatic hydrocarbyl includes, but is not limited to 6-12 membered aromatic hydrocarbyl such as benzene and naphthalene. In some embodiments, the term "hydrocarbyl" refers to a linear or branched atomic group or a combination thereof, which may be fully saturated, mono-unsaturated or poly-unsaturated, and may include divalent and polyvalent atomic groups. Examples of saturated hydrocarbon atomic groups include, but are not limited to, methyl, ethyl, n-propyl, isopropyl, n-butyl, tert-butyl, isobutyl, sec-butyl, isobutyl, cyclohexyl, (cyclohexyl)methyl, cyclopropylmethyl, and homologs or isomers of atomic groups such as n-pentyl, n-hexyl, n-heptyl and n-octyl. Unsaturated hydrocarbyl has one or more double bonds or triple bonds, and examples thereof include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologs and isomers.

Unless otherwise specified, the term "heterohydrocarbyl" or its subordinate concept (such as heteroalkyl, heteroalkenyl, heteroalkynyl and heteroaryl) by itself or in combination with another term means a stable linear, branched or cyclic hydrocarbon atomic group consisting of a certain number of carbon atoms and at least one heteroatom, or a combination thereof. In some embodiments, the term "heteroalkyl" by itself or in combination with another term means a stable linear or branched alkyl atomic group consisting of a certain number of carbon atoms and at least one heteroatom, or a combination thereof. In a typical embodiment, the heteroatom is selected from B, O, N and S, wherein the nitrogen and sulfur atoms are optionally oxidized, and the nitrogen heteroatom is optionally quaternized. Heteroatom or heteroatomic group may be located at any internal position of heterohydrocarbyl, including the connection positions of the hydrocarbyl to the remainder of the molecule. However, the terms "alkoxy", "alkylamino" and "alkylthio" (or thioalkoxy) are used in their conventional sense and refer to those alkyl groups attached to the remainder of the molecule via an oxygen atom, an amino group, or a sulfur atom, respectively. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CHO—CH$_3$, —CH$_2$—CH=N—OCH$_3$ and —CH=CH—N(CH$_3$)—CH$_3$. Up to two heteroatoms can be consecutive, such as —CH2-NH—OCH$_3$.

Unless otherwise specified, the term "cyclohydrocarbyl", "heterocyclohydrocarbyl" or its subordinate concept (such as aryl, heteroaryl, cycloalkyl, heterocycloalkyl, cycloalkenyl, heterocycloalkenyl, cycloalkynyl and heterocycloalkynyl) by itself or in combination with other terms means cyclized "hydrocarbyl" and "heterohydrocarbyl", respectively. In addition, as far as heterohydrocarbyl or heterocyclohydrocarbyl (such as heteroalkyl and heterocycloalkyl), heteroatoms can occupy the position where the heterocycle is attached to the remainder of the molecule. Examples of cyclohydrocarbyl include, but are not limited to, cyclopentyl, cyclohexyl, 1-cyclohexenyl, 3-cyclohexenyl, cycloheptyl, etc. Non-limiting examples of heterocyclyl include 1-(1,2,5,6-tetrahydropyridyl), 1-piperidyl, 2-piperidyl, 3-piperidyl, 4-morpholinyl, 3-morpholinyl, tetrahydrofuran-2-yl, tetrahydrofuran indol-3-yl, tetrahydrothiophen-2-yl, tetrahydrothiophen-3-yl, 1-piperazinyl and 2-piperazinyl.

Unless otherwise specified, the term "alkyl" is used to represent a linear or branched saturated hydrocarbyl, which may be mono-substituted (such as —CH$_2$F) or poly-substituted (such as —CF$_3$), and may be monovalent (such as methyl), divalent (such as methylene) or polyvalent (such as methine). Examples of alkyl include methyl (Me), ethyl (Et), propyl (e.g., n-propyl and isopropyl), butyl (e.g., n-butyl, isobutyl, s-butyl and t-butyl), pentyl (e.g., n-pentyl, isopentyl and neopentyl), etc.

Unless otherwise specified, "alkenyl" refers to alkyl having one or more carbon-carbon double bonds at any position on the chain, which may be mono-substituted or poly-substituted, and may be monovalent, divalent, or polyvalent. Examples of alkenyl include vinyl, propenyl, butenyl, pentenyl, hexenyl, butadienyl, pentadienyl, hexadienyl, etc.

Unless otherwise specified, cycloalkyl includes any stable cyclic or polycyclic hydrocarbyl, in which any carbon atom is saturated, and may be mono-substituted or poly-substituted, and may be monovalent, divalent, or polyvalent. Examples of the cycloalkyl include, but are not limited to, cyclopropyl, norbornyl, [2.2.2] bicyclooctane, [4.4.0]bicyclodecane etc.

Unless otherwise specified, cycloalkenyl includes any stable cyclic or polycyclic hydrocarbyl containing one or more unsaturated carbon-carbon double bonds at any position on the ring, which may be mono-substituted or poly-substituted, and may be monovalent, divalent, or polyvalent. Examples of the cycloalkenyl include, but are not limited to, cyclopentenyl, cyclohexenyl, etc.

Unless otherwise specified, the term "halo" or "halogen" by itself or as part of another substituent means a fluorine, chlorine, bromine or iodine atom. In addition, the term "haloalkyl" is intended to include monohaloalkyl and polyhaloalkyl. For example, the term "halo($C_1$-$C_4$)alkyl" is intended to include, but is not limited to, trifluoromethyl, 2,2,2-trifluoroethyl, 4-chlorobutyl, 3-bromopropyl, etc. Unless otherwise specified, examples of haloalkyl include, but are not limited to: trifluoromethyl, trichloromethyl, pentafluoroethyl and pentachloroethyl.

Unless otherwise specified, the term "alkoxy" represents the above-mentioned alkyl having a specific number of carbon atoms connected via an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but are not limited to: methoxy, ethoxy, n-propoxy, isopropoxy, n-butoxy, sec-butoxy, tert-butoxy, n-pentoxy and S-pentoxy.

Unless otherwise specified, the term "aryl" means a poly-unsaturated aromatic hydrocarbon substituent, which may be mono-substituted or poly-substituted, may be mono-ovalent, divalent or polyvalent, and may be monocyclic or polycyclic (e.g., 1 to 3 rings, wherein at least one of the rings is aromatic), which are fused together or covalently linked. The term "heteroaryl" refers to aryl (or ring) containing one to four heteroatoms. In an exemplary example, the heteroatom is selected from B, N, O, and S, wherein the nitrogen and sulfur atoms are optionally oxidized, and the nitrogen atom is optionally quaternized. Heteroaryl can be connected to the remainder of the molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furyl, thienyl, pyridyl, pyrimidinyl, benzothiazolyl, purinyl, benzimidazolyl, indolyl, isoquinolinyl, quinoxalinyl, quinolinyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl and 6-quinolinyl. The substituent of any one of the above-mentioned aryl and heteroaryl ring systems is selected from the acceptable substituents described below.

Unless otherwise specified, aryl when used in combination with other terms (e.g., aryloxy, arylthio and aralkyl) includes aryl and heteroaryl rings as defined above. Therefore, the term "aralkyl" is intended to include those atomic groups where aryl is attached to alkyl (e.g., benzyl, phenethyl, pyridylmethyl, etc.), including those alkyl groups in which carbon atoms (such as methylene) have been replaced by, for example, oxygen atoms, such as phenoxymethyl and 2-pyridyloxymethyl 3-(1-naphthyloxy)propyl.

The term "protecting group" includes, but is not limited to, "amino protecting group", "hydroxy protecting group" or "mercapto protecting group". The term "amino protecting group" refers to a protecting group suitable for preventing side reactions occurring at the nitrogen atom of an amino group. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl)methyl; silyl, such as trimethylsilyl (TMS) and tert-butyldimethylsilyl (TBS). The term "hydroxyl protecting group" refers to a protecting group suitable for preventing side reactions of a hydroxyl group. Representative hydroxyl protecting groups include, but are not limited to: alkyl, such as methyl, ethyl and tert-butyl; acyl, such as alkanoyl (e.g., acetyl); arylmethyl, such as benzyl (Bn), p-methoxybenzyl (PMB), 9-fluorenylmethyl (Fm) and diphenylmethyl (DPM); silyl, such as trimethylsilyl (TMS) and tert-butyldimethylsilyl (TBS).

The term "post-treatment" means that the formate, hydrochloride or trifluoroacetate salt of the compound of the present disclosure is dissolved in an organic solvent such as ethyl acetate, dichloromethane or methanol, washed with 1 N sodium bicarbonate solution, and subjected to the organic phase concentration method to obtain the free state of the compound.

The compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

The solvents used in the present disclosure are commercially available. The present disclosure uses the following abbreviations: aq represents water; T3P represents 1-n-propyl phosphoric anhydride; eq represents equivalent; DCM represents dichloromethane; PE represents petroleum ether; DMF represents N,N-dimethylformamide; DMSO represents dimethyl sulfoxide; EtOAc represents ethyl acetate; EtOH represents ethanol; MeOH represents methanol; ACN represents acetonitrile; CBz represents benzyloxycarbonyl, which is an amine protecting group; BOC represents tert-butoxycarbonyl, which is an amine protecting group; r.t. represents room temperature; O/N represents overnight; THF represents tetrahydrofuran; $Boc_2O$ represents di-tert-butyl dicarbonate; TFA represents trifluoroacetic acid; HCl represents hydrochloric acid; DIPEA represents diisopropylethylamine; mp represents melting point; $Pd(PPh_3)_2Cl_2$ represents bis(triphenylphosphine)palladium dichloride; $pd(dppf)Cl_2$ represents [1,1'-bis(diphenylphosphino)ferrocene]palladium dichloride.

Compounds are named by hand or ChemDraw® software, and commercially available compounds are named by the supplier catalog names.

Technical Effects

The compounds of the present disclosure have good GLS1 enzyme inhibitory activity, significant anti-tumor effect, and potential application value in the treatment of diseases related to cell proliferation. The compounds of the present disclosure have good solubility and permeability, good in vivo metabolic stability, high in vivo exposure and high bioavailability, and are potential pharmaceutical compounds.

BRIEF DESCRIPTION OF THE DRAWINGS

FIG. 1 shows the relative weight change (%) of the test substance in a female CB-17 SCID subcutaneously transplanted tumor model of human myeloma RPMI-8226 cells.

IP: Intraperitoneal injection; PO: Oral administration; QW: Once a week; QD: Once a day; BID: Twice a day.

The relative weight change is calculated based on the weight of the animal at the beginning of the administration. The data points represent the average weight change percentage within the group, and the error bars represent the standard error (SEM).

DETAILED DESCRIPTION OF THE PREFERRED EMBODIMENT

The present disclosure will be described in detail with the following examples, but not imply any adverse limitation to the present disclosure. The present disclosure has been described in detail herein, and the specific embodiments thereof are also disclosed therein.

For a person skilled in the art, without departing from the spirit and scope of the present disclosure, all the variations and improvements made to the specific embodiments of the present disclosure would have been obvious.

Intermediate 1-7

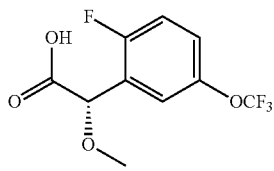 [SMILES: CO[C@H](C(=O)O)c1cc(OC(F)(F)F)ccc1F]

Synthetic Route:

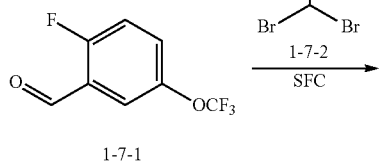

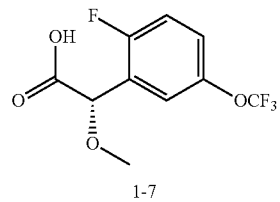

Step 1: Compound potassium hydroxide (3.25 g, 57.86 mmol) was added to methanol (30 mL), and then the mixture was slowly added dropwise to a mixed solution of compound 1-7-1 (2 g, 9.61 mmol) and compound 1-7-2 (3.19 g, 12.62 mmol) in methanol (20 mL) at 0° C., and the reaction solution was stirred at 25° C. for 19 hours. After completion of the reaction, the reaction solution was extracted with tert-butyl methyl ether (100 mL) and water (100 mL). The aqueous phase was acidified with dilute hydrochloric acid to pH=5, and then extracted with ethyl acetate (20 mL*3). The organic phase was washed with saturated brine (80 mL), dried over anhydrous sodium sulfate, concentrated, and then subjected to resolution by column chromatography (dichloromethane:methanol=10:1), followed by supercritical fluid chromatography (chromatographic column: ChiralPak IC-3 150×4.6 mm I.D., 5 m; mobile phase: A: $CO_2$ B: isopropanol (0.05% DEA); gradient: 5%-40%; flow rate: 2.5 mL/min; column temperature: 40° C.; elution time: 10.0 min) to obtain compound 1-7 with the retention time of 3.28 min. 1H NMR (400 MHz, $CDCl_3$) δ ppm 3.43 (s, 3H), 5.03 (s, 1H), 7.02-7.10 (m, 1H), 7.12-7.18 (m, 1H), 7.26 (dd, J=2.89, 5.14 Hz, 1H), 10.38 (brs, 1H).

Examples 1 and 2: Preparations of Compounds 1 and 2

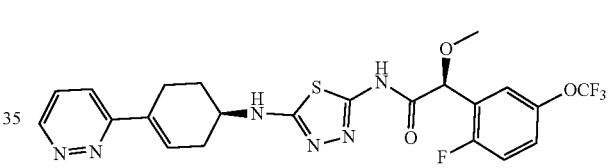

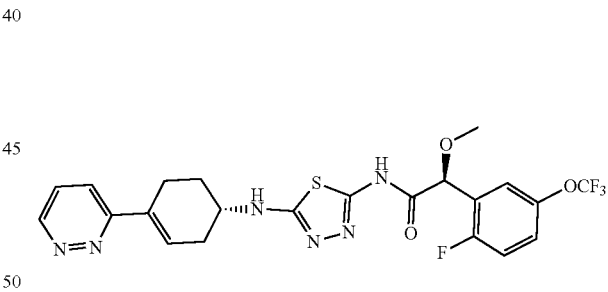

Synthetic Route:

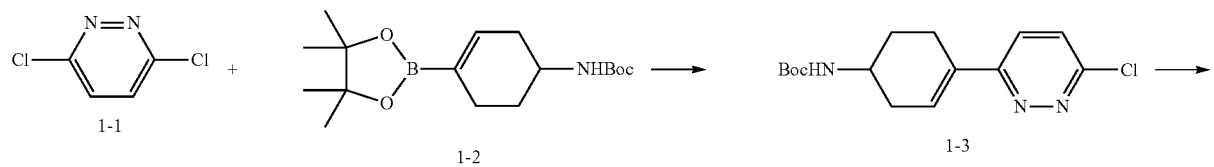

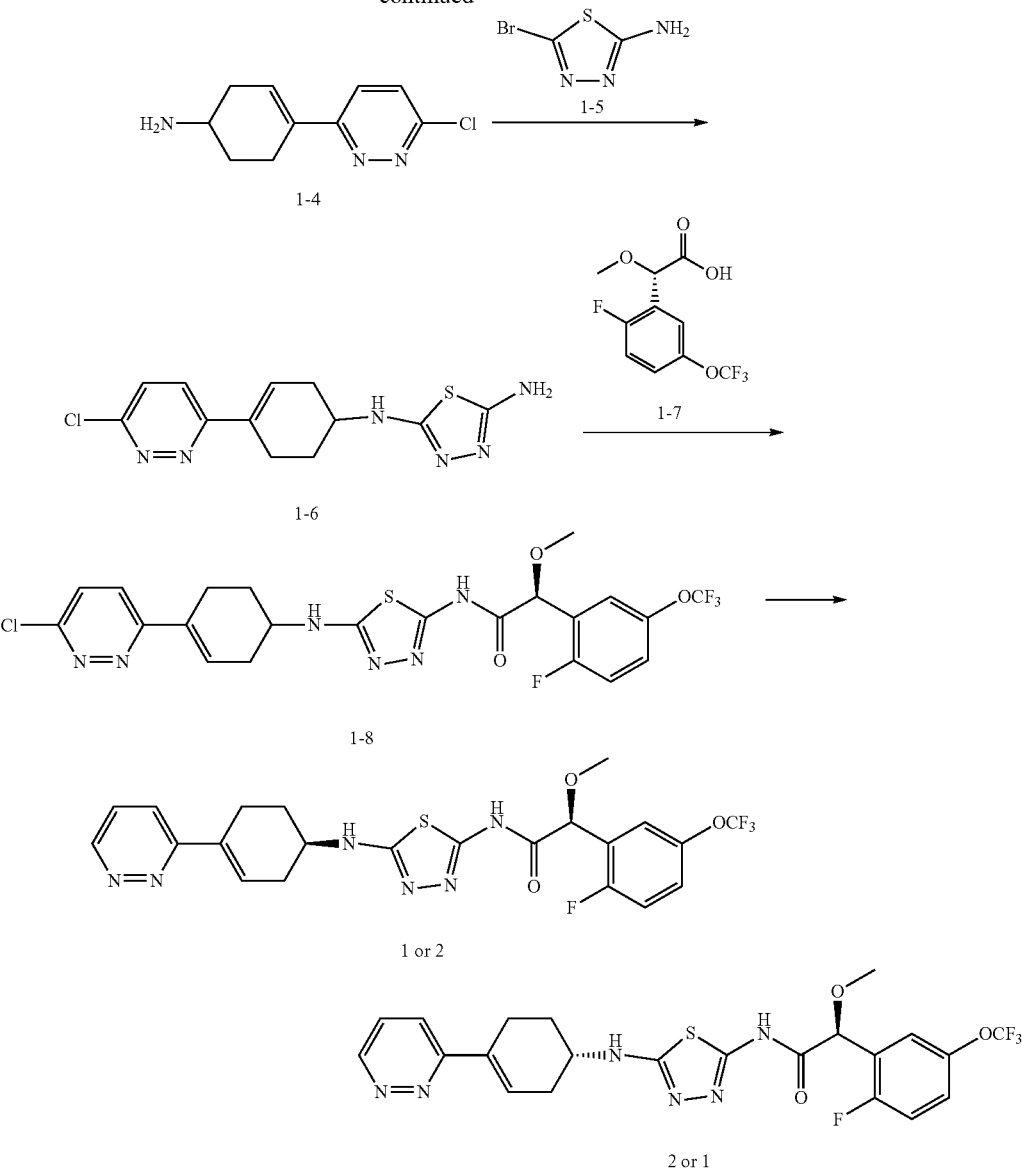

Step 1: Compound 1-1 (1.50 g, 10.07 mmol), compound 1-2 (3.25 g, 10.07 mmol), Pd(dppf)Cl$_2$ (822.24 mg, 1.01 mmol) and potassium carbonate (4.17 g, 30.21 mmol) were added to 1,4-dioxane (30 mL) and water (12 mL), and the reaction solution was stirred at 80° C. for 2 hours under nitrogen protection. After completion of the reaction, the reaction solution was extracted with ethyl acetate (30 mL*3), and the organic phase was dried over anhydrous sodium sulfate, filtered and then evaporated to dryness. The residue was purified by silica gel column chromatography (ethyl acetate/petroleum ether=1:5) to obtain compound 1-3. MS ESI calculated value for C$_{15}$H$_{20}$ClN$_3$O$_2$[M+H]$^+$ 310, measured value 310.

Step 2: Compound 1-3 (3.0 g, 9.68 mmol) was added to HCl/MeOH (30 mL, 4 M), and the mixture was stirred at 25° C. for 1 hour. After completion of the reaction, the reaction solution was evaporated to remove the solvent to obtain compound 1-4, which was directly used in the next reaction. MS ESI calculated value for C$_{10}$H$_{12}$ClN$_3$ [M+H]$^+$ 210, measured value 210.

Step 3: Compound 1-4 (2.0 g, 9.54 mmol) and compound 1-5 (1.72 g, 9.54 mmol) were dissolved in ethanol (30 mL), and sodium bicarbonate (4.81 g, 57.23 mmol) was added thereto. The reaction solution was stirred at 80° C. for 6 hours. The reaction solution was filtered and evaporated to dryness, and the residue was purified by silica gel column chromatography (DCM/MeOH=10:1) to obtain compound 1-6. MS ESI calculated value for C$_{12}$H13ClN$_6$S [M+H]$^+$ 309, measured value 309.

Step 4: Compound 1-6 (0.8 g, 2.59 mmol) and compound 1-7 (0.69 g, 2.59 mmol) were dissolved in DMF (20 mL), and then diisopropylethylamine (502.25 mg, 3.89 mmol) and 1-n-propyl phosphoric anhydride-(2.47 g, 3.89 mmol, 50% solution in ethyl acetate) were added thereto successively. The reaction solution was stirred at 25° C. for 4 hours. The reaction solution was distilled under reduced pressure to remove the solvent, and the residue was purified by silica gel column chromatography (DCM/MeOH=10:1) to obtain compound 1-8. MS ESI calculated value for C$_{22}$H$_{19}$ClF$_4$N$_6$O$_3$S [M+H]$^+$ 559, measured value 559.

Step 5: Compound 1-8 (0.5 g, 0.89 mmol) was added to methanol (50 mL), and then dry palladium on carbon (10% purity, 0.05 g) and ammonium formate (0.34 g, 5.37 mmol) were added thereto. The reaction solution was stirred at 40° C. for 1 hour under nitrogen protection. The reaction solution was filtered, and the filtrate was concentrated to obtain a residue. The residue was purified by silica gel column chromatography (DCM/MeOH=10:1) and then resolved by supercritical fluid chromatography (chromatographic column: Chiralcel OJ-H 150*4.6 mm I.D., 5 m; mobile phase: A: $CO_2$ B: ethanol (0.05% DEA); gradient: 5% to 40%; flow rate: 3 mL/min; column temperature: 40° C.; elution time: 8.0 min) to obtain compound 1 and compound 2.

The retention time of compound 1 was 3.52 min; MS ESI calculated value for $C_{22}H_{20}F_4N_6O_3S$ [M+H]$^+$ 525, measured value 525.

The retention time of compound 2 was 3.94 min; MS ESI calculated value for $C_{22}H_{20}F_4N_6O_3S$ [M+H]$^+$ 525, measured value 525. $^1$HNMR (400 MHz, MeOD) δ ppm 1.80-1.93 (m, 1H), 2.24-2.38 (m, 2H), 2.80-2.86 (m, 3H), 3.46 (s, 3H), 4.02-4.05 (m, 1H), 5.22 (s, 1H), 6.75 (d, J=18.80 Hz, 1H), 7.30-7.48 (m, 3H), 7.66 (dd, J=8.80 Hz & 4.80 Hz, 1H), 7.97-8.02 (m, 1H), 9.03 (d, J=4.02 Hz, 1H).

Examples 3 and 4: Preparations of Compounds 3 and 4

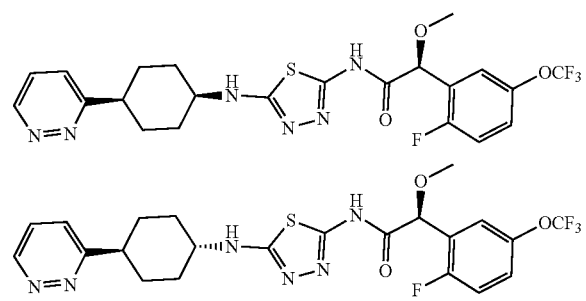

Synthetic Route:

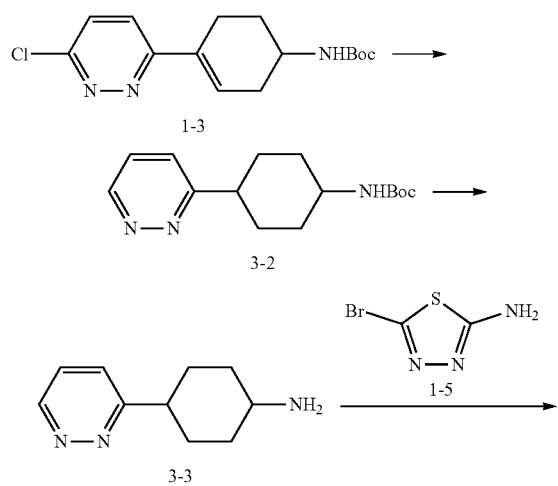

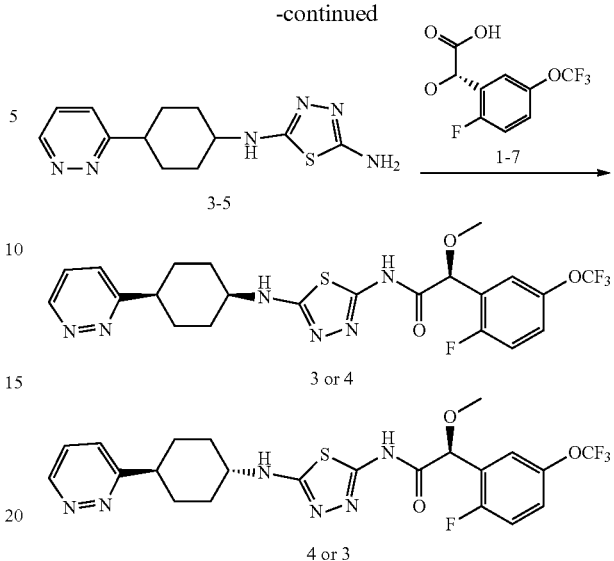

Step 1: Compound 1-3 (1.7 g, 5.49 mmol) was added to methanol (30 mL), and then dry palladium on carbon (10% purity, 0.2 g) was added thereto. The reaction solution was replaced with hydrogen twice and stirred at 25° C. for 12 hours under 15 psi hydrogen. The reaction solution was filtered, and evaporated to remove the solvent. The residue was purified by preparative thin layer chromatography sheet (petroleum ether: ethyl acetate=1:1) to obtain compound 3-2. MS ESI calculated value for $C_{15}H_{23}N_3O_2$ [M+H]$^+$ 278, measured value 278.

Step 2: Compound 3-2 (0.2 g, 721.08 μmol) was added to HCl/MeOH (10 mL, 4 M), and the mixture was stirred at 25° C. for 0.5 hours. After completion of the reaction, the reaction solution was evaporated to dryness to obtain compound 3-3. MS ESI calculated value for $C_{10}H_{15}N_3$[M+H]$^+$ 178, measured value 178.

Step 3: Compound 3-3 (0.127 g, 0.72 mmol), and compound 1-5 (0.129 g, 0.72 mmol) were dissolved in ethanol (5 mL), and sodium bicarbonate (0.361 g, 4.3 mmol) was added thereto. The reaction solution was stirred at 80° C. for 6 hours. The reaction solution was filtered, and evaporated to remove the solvent. The residue was purified by preparative thin layer chromatography sheet (DCM/MeOH=10:1) to obtain compound 3-5. MS ESI calculated value for $C_{12}H_{16}N_6S$ [M+H]$^+$ 277, measured value 277.

Step 4: Compound 3-5 (0.15 g, 542.77 μmol) and compound 1-7 (145.55 mg, 542.77 mol) were dissolved in DMF (5 mL), and then DIEA (105.22 mg, 814.16 μmol) and T3P (518.10 mg, 814.16 μmol, 484.20, 50% solution in ethyl acetate) were added thereto successively. The reaction solution was stirred at 25° C. for 2 hours. The reaction solution was evaporated under reduced pressure to remove the solvent, and the residue was purified by preparative thin layer chromatography (DCM/MeOH=10:1) to obtain compound 3 and compound 4.

The Rf of compound 3 was 0.45; MS ESI calculated value for $C_{26}H_{25}F_3N_8O_3$[M+H]$^+$ 527, measured value 527. $^1$HNMR (400 MHz, MeOD) δ ppm 1.82-1.89 (m, 4H), 2.00-2.14 (m, 4H), 3.05-3.16 (m, 1H), 3.48 (s, 3H), 4.07-4.11 (m, 1H), 5.28 (s, 1H), 7.28-7.38 (m, 2H), 7.47 (d, J=5.20 Hz, 1H), 7.69-7.71 (m, 2H), 9.03 (dd, J=5.20 Hz & 2.02 Hz, 1H)

The Rf of compound 4 was 0.38; MS ESI calculated value for $C_{26}H_{25}F_3N_8O_3$ [M+H]$^+$ 527, measured value 527.

Example 5: Preparation of Compound 5 (Hydrochloride Salt)

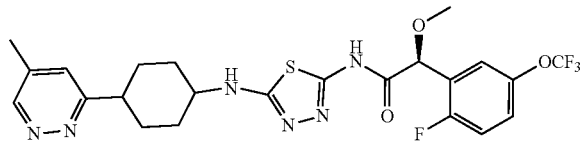 [SMILES: CO[C@H](C(=O)Nc1nnc(NC2CCC(c3cc(C)cnn3)CC2)s1)c1cc(OC(F)(F)F)ccc1F]

Synthetic Route:

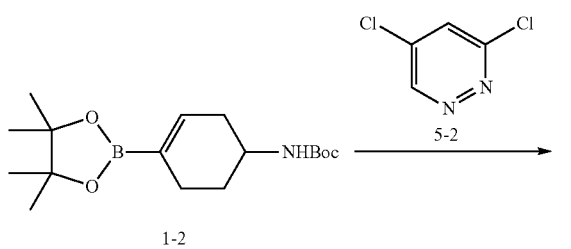

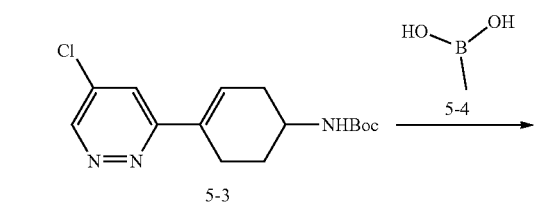

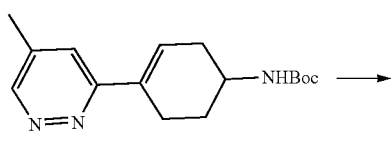

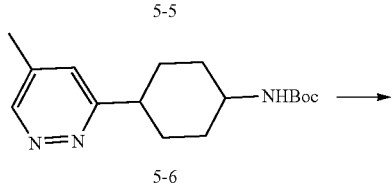

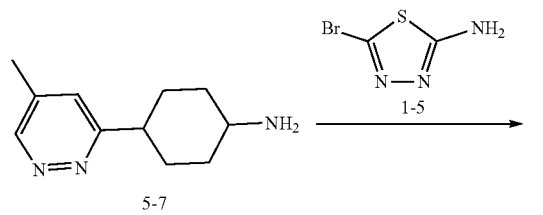

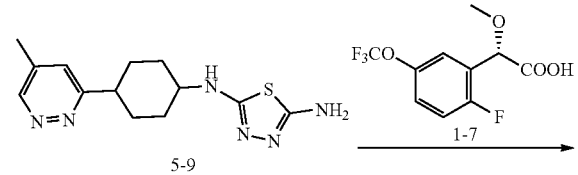

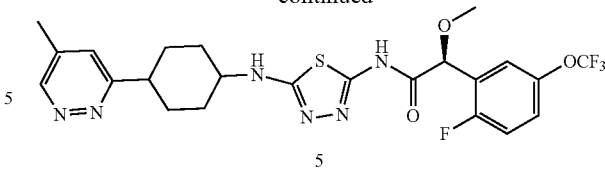

Step 1: Compound 1-2 (4.77 g, 14.77 mmol), compound 5-2 (2 g, 13.42 mmol) and potassium carbonate (5.57 g, 40.27 mmol) were added to dioxane (35 mL) and water (14 mL). Then Pd(dppf)Cl$_2$ (982.30 mg, 1.34 mmol) was added, and the reaction solution was heated to 80° C. and stirred for 1 hour under nitrogen protection. After completion of the reaction, the reaction solution was filtered, and the filtrate was evaporated to dryness. Water (100 mL) was added, and then the solution was extracted with ethyl acetate (100 mL*3). The organic phase was washed with saturated brine (80 mL) and dried over anhydrous sodium sulfate, filtered and evaporated to remove the solvent. The residue was purified by column chromatography (petroleum ether/ethyl acetate=1:1) to obtain compound 5-3. MS ESI calculated value for $C_{15}H_{20}ClN_3O_2$[M+H]$^+$ 310, measured value 310.

Step 2: Compound 5-3 (0.2 g, 645.60 μmol) and compound 5-4 (154.58 g, 2.58 mmol) were added to dioxane (2.5 mL) and water (1 mL). Then Pd(dppf)Cl$_2$ (23.62 mg, 32.28 μmol), cesium carbonate (420.70 mg, 1.29 mmol) and 2-dicyclohexylphosphino-2,4,6-triisopropylbiphenyl (307.77 mg, 645.60 μmol) were added, and the reaction solution was heated to 80° C. and stirred for 16 hours under nitrogen protection. After completion of the reaction, the reaction solution was filtered, and the filtrate was evaporated to dryness. Water (100 mL) was added, and then the solution was extracted with ethyl acetate (100 mL*3). The organic phase was washed with saturated brine (80 mL) and dried over anhydrous sodium sulfate, filtered and evaporated to remove the solvent. The residue was separated by column chromatography (petroleum ether/ethyl acetate=1:1) to obtain compound 5-5. MS ESI calculated value for $C_{16}H_{23}N_3O_2$ [M+H]$^+$ 290, measured value 290.

Step 3: Compound 5-5 (0.1 g, 345.58 μmol) was added to MeOH (5 mL), and then palladium on carbon (0.02 g, 10% purity) was added thereto under nitrogen. The reaction was carried out at 40° C. for 30 minutes under 15 psi hydrogen. The reaction solution was filtered, and the filtrate was evaporated to dryness to obtain compound 5-6, which was directly used in the next reaction. MS ESI calculated value for $C_{16}H_{25}N_3O_2$ [M+H]$^+$ 292, measured value 292.

Step 4: Compound 5-6 (0.04 g, 137.27 μmol) was dissolved in TFA (5 mL) and DCM (5 mL), and the reaction solution was stirred at 25° C. for 5 minutes. The reaction solution was evaporated to remove the solvent to obtain compound 5-7. MS ESI calculated value for $C_{11}H_{17}N_3$[M+H]$^+$ 192, measured value 192.

Step 5: Compound 5-7 (27.90 g, 141.16 μmol) and compound 1-5 (25.41 g, 141.16 mol) were dissolved in ethanol (5 mL), and sodium bicarbonate (71.15 g, 846.96 μmol) was added thereto. The reaction solution was stirred at 90° C. for 16 hours. The reaction solution was filtered, and the filtrate was evaporated to dryness to obtain compound 5-9, and the crude product was directly used in the next reaction. MS ESI calculated value for $C_{13}H_{18}N_6S$ [M+H]$^+$ 291, measured value 291.

Step 6: Compound 5-9 (0.05 g, 172.18 μmol) and compound 1-7 (0.03 g, 111.87 μmol) were dissolved in DMF (5 mL), and then T3P (106.79 mg, 167.81 μmol, 99.80 μL, 50% purity) and DIEA (167.81 μmol, 29.23 μL) were added thereto successively. The reaction solution was stirred at 40° C. for 1 hour. After completion of the reaction, a saturated sodium bicarbonate aqueous solution (50 mL) was added, and the solution was then extracted with ethyl acetate (50 mL*3). The organic phase was washed with saturated brine (30 mL), dried over anhydrous sodium sulfate, filtered and evaporated to remove the solvent. The residue was separated by preparative high performance liquid chromatography (chromatographic column: YMC-Actus Triart C18 100*30 mm*5 m; mobile phase: water (0.05% HCl)-ACN; B (acetonitrile) %: 40%-70%, 10 min) to obtain the hydrochloride salt of compound 5. MS ESI calculated value for $C_{23}H_{24}F_4N_6O_3S$ [M+H]$^+$ 541, measured value 541. The hydrochloride salt of compound 5 was subjected to post-processing to obtain compound 5.

Example 6: Preparation of Compound 6 (Hydrochloride Salt)

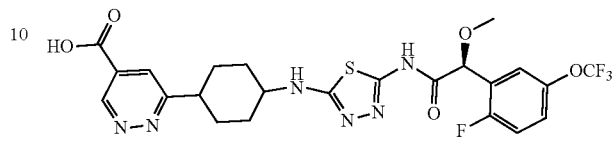

Synthetic Route:

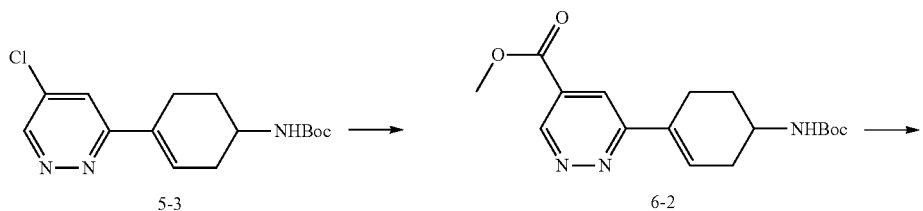

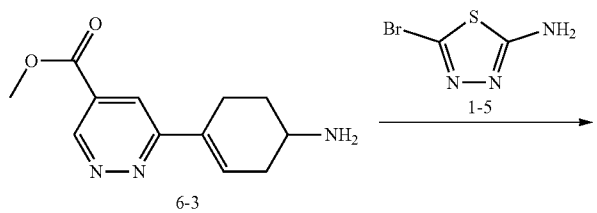

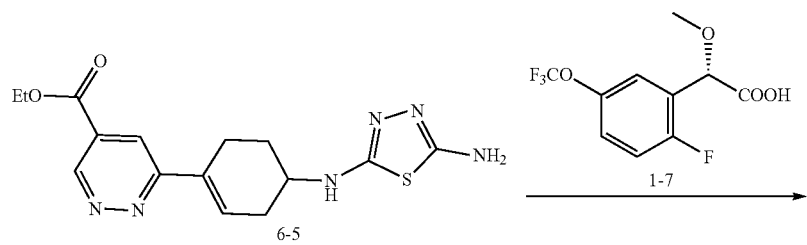

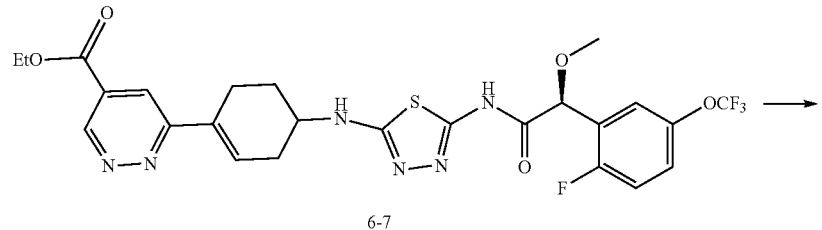

-continued

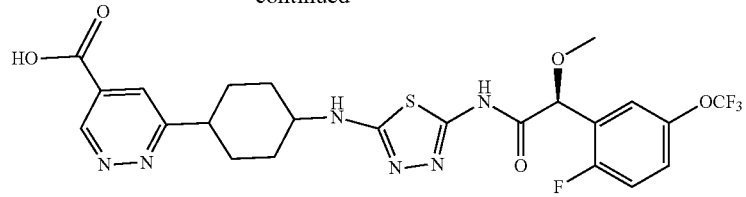

6

Step 1: Compound 5-3 (0.2 g, 645.60 μmol) was dissolved in dimethyl sulfoxide (8 mL) and methanol (2 mL), and then palladium acetate (7.25 mg, 32.28 μmol), 1,3-bisdiphenylphosphine propane (26.63 mg, 64.56 μmol) and triethylamine (97.99 mg, 968.40 mol, 134.79 μL) were added thereto. The reaction solution was stirred at 80° C. for 16 hours under 50 psi carbon monoxide. After completion of the reaction, the reaction solution was filtered, and the filtrate was evaporated to dryness. Water (10 mL) was added, and then the solution was extracted with ethyl acetate (15 mL*3). The organic phase was washed with saturated brine (5 mL), dried over anhydrous sodium sulfate, filtered and evaporated to remove the solvent. The residue was separated by preparative thin layer chromatography sheet (petroleum ether/ethyl acetate=1:1) to obtain compound 6-2. MS ESI calculated value for $C_{17}H_{23}N_3O_4$ $[M+H]^+$ 334, measured value 334.

Step 2: Compound 6-2 (0.1 g, 299.96 μmol) was dissolved in TFA (5 mL) and DCM (5 mL), and the mixture was stirred at 25° C. for 5 minutes. After completion of the reaction, the reaction solution was evaporated to remove the solvent to obtain compound 6-3. MS ESI calculated value for $C_{12}H_{15}N_3O_2$ $[M+H]^+$ 234, measured value 234.

Step 3: Compound 6-3 (0.07 g, 300.09 μmol) and compound 1-5 (54.02 g, 300.09 mol) were dissolved in ethanol (5 mL), and sodium bicarbonate (151.26 mg, 1.80 mmol, 70.03 L) was added thereto. The reaction solution was stirred at 90° C. for 16 hours. The reaction solution was filtered, and evaporated to remove the solvent to obtain a crude product of compound 6-5. MS ESI calculated value for $C_{15}H_{18}N_6S$ $[M+H]^+$ 347, measured value 347.

Step 4: Compound 6-5 (100 mg, crude) and compound 1-7 (478.66 mg, 1.78 mmol) were dissolved in DMF (5 mL), and then T3P (1.70 g, 2.68 mmol, 1.59 mL, 50% purity) and diisopropylethylamine (346.04 mg, 2.68 mmol, 466.35 μL) were added thereto. The reaction solution was stirred at 40° C. for 1 hour. After completion of the reaction, a saturated sodium bicarbonate aqueous solution (10 mL) was added, and the solution was then extracted with ethyl acetate (50 mL*3). The organic phase was washed with saturated brine (20 mL), dried over anhydrous sodium sulfate, filtered and evaporated to remove the solvent. The residue was separated by preparative thin layer chromatography sheet (dichloromethane/methanol=10:1) to obtain compound 6-7. MS ESI calculated value for $C_{25}H_{24}F_4N_6O_5S$ $[M+H]^+$ 597, measured value 597.

Step 5: Compound 6-7 (0.02 g, 33.53 μmol) was added to MeOH (5 mL), and then palladium on carbon (0.02 g, 10% purity) was added thereto under nitrogen. The reaction was carried out at 40° C. for 10 minutes under 15 psi hydrogen. The reaction solution was filtered, and the filtrate was evaporated to dryness to obtain compound 6-8. MS ESI calculated value for $C_{25}H_{26}F_4N_6O_5S$ $[M+H]^+$ 599, measured value 599.

Step 6: Compound 6-8 (0.01 g, 16.71 μmol) was dissolved in tetrahydrofuran (2 mL), methanol (2 mL) and water (1 mL), and lithium hydroxide monohydrate (12.33 mg, 293.83 mol) was added thereto. The reaction solution was stirred at 25° C. for 1 hour. The reaction solution was filtered, and the filtrate was evaporated to dryness. The residue was separated by preparative high performance liquid chromatography (chromatographic column: YMC-Actus Triart C18 100*30 mm*5 m; mobile phase: [water (0.05% HCl)-ACN]; B (acetonitrile) %: 30%-60%, 10 min) to obtain the hydrochloride salt of compound 6. MS ESI calculated value for $C_{23}H_{22}F_4N_6O_5S$ $[M+H]^+$ 571, measured value 571. The hydrochloride salt of compound 6 was subjected to post-processing to obtain compound 6.

Example 7: Preparation of Compound 7 (Hydrochloride Salt)

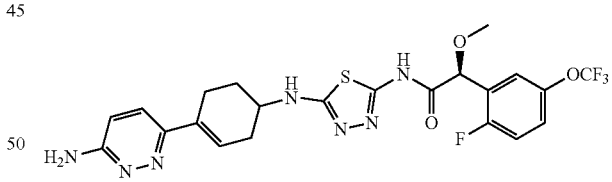

Synthetic Route:

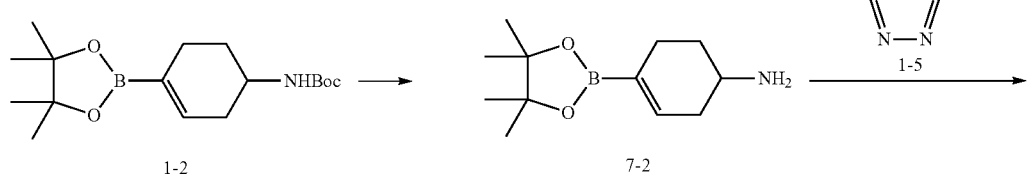

1-2                                        7-2

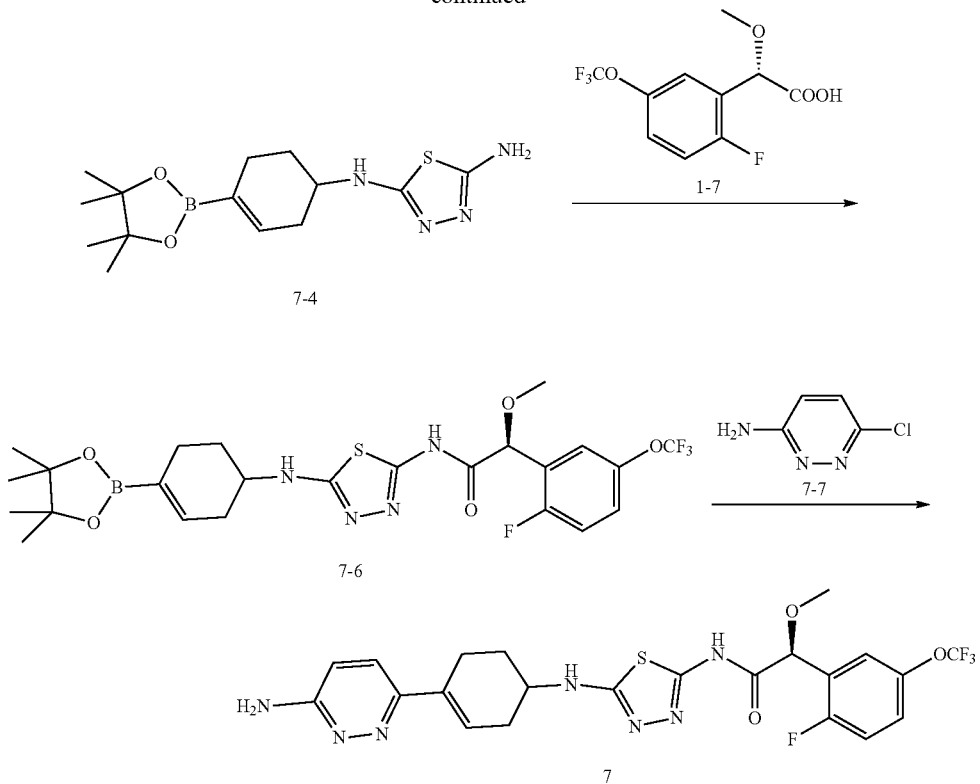

Step 1: Compound 7-1 (0.9 g, 137.27 μmol) was dissolved in TFA (2 mL) and DCM (5 mL), and the reaction solution was stirred at 30° C. for 15 minutes. The reaction solution was evaporated to remove the solvent to obtain compound 7-2. MS ESI calculated value for $C_{12}H_{22}BNO_2$ [M+H]$^+$ 224, measured value 224.

Step 2: Compound 7-2 (0.94 g, 2.79 mmol) and compound 1-5 (0.53 g, 2.93 mmol) were dissolved in DMF (10 mL), and DIEA (0.72 g, 5.58 mmol) was added thereto. The reaction solution was stirred at 100° C. for 1 hour, which was used directly in the next step.

Compound 7-4. MS ESI calculated value for $C_{14}H_{23}BN_4O_2S$ [M+H]$^+$ 323, measured value 323.

Step 3: To a solution of compound 7-4 in DMF (10 mL) were added compound 1-7 (0.20 g, 0.75 mmol) and diisopropylethylamine (0.19 g, 1.49 mmol), and then T3P (0.44 mL, 1.49 mmol, 50% purity) was added thereto. The reaction solution was stirred at 40° C. for 1 hour. After completion of the reaction, the reaction solution was evaporated under reduced pressure to remove the solvent. The residue was dissolved in ethyl acetate (100 mL), and washed with a saturated sodium bicarbonate aqueous solution (20 mL), water (20 mL), and saturated brine (20 mL) successively. The organic phase was dried over anhydrous sodium sulfate, filtered and evaporated to remove the solvent. The residue was separated by preparative thin layer chromatography (dichloromethane/methanol=10:1) to obtain compound 7-6. MS ESI calculated value for $C_{24}H_{29}BF_4N_4O_5S$ [M+H]$^+$ 573, measured value 573.

Step 4: Compound 7-6 (331.37 mg, 0.58 mmol), compound 7-7 (0.15 g, 1.16 mmol) and potassium carbonate (160.03 mg, 1.16 mmol) were added to dioxane (6 mL) and water (1.5 mL). Then Pd(dppf)Cl$_2$ (84.72 mg, 0.12 mmol) was added, and the reaction solution was heated to 90° C. and stirred for 10 minutes under nitrogen protection. After completion of the reaction, water (20 mL) was added, and the solution was then extracted with ethyl acetate (50 mL*2). The organic phase was washed with saturated brine (10 mL), dried over anhydrous sodium sulfate, filtered and evaporated to remove the solvent. The residue was purified by preparative thin layer chromatography sheet (dichloromethane/methanol=20:1) and preparative high performance liquid chromatography (chromatographic column: YMC-Actus Triart C18 100*30 mm*5 m; mobile phase: [water (0.05% HCl)-ACN]; B (acetonitrile) %: 35%-54%, 7 min) successively to obtain the hydrochloride salt of compound 7. MS ESI calculated value for $C_{22}H_{21}F_4N_7O_3S$ [M+H]$^+$ 540, measured value 540. $^1$HNMR (400 MHz, MeOD) δ ppm 1.93-2.14 (m, 1H), 2.45-2.48 (m, 1H), 2.50-2.57 (m, 1H), 2.65-2.76 (m, 3H), 3.48 (s, 3H), 3.97-4.02 (m, 1H), 5.34 (s, 1H), 6.76 (d, J=11.6 Hz, 1H), 7.12 (d, J=9.6 Hz, 1H), 7.30 (d, J=9.6 Hz, 1H), 7.39-7.50 (m, 3H), 8.22 (d, J=9.6 Hz, 1H). The hydrochloride salt of compound 7 was subjected to post-processing to obtain compound 7.

Example 8: Preparation of Compound 8 (Trifluoroacetate Salt)

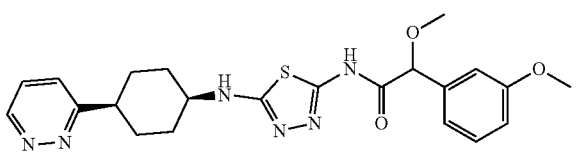 [SMILES: COc1cccc(C(OC)C(=O)Nc2nnc(N[C@H]3CC[C@@H](c4cccnn4)CC3)s2)c1]

Synthetic Route:

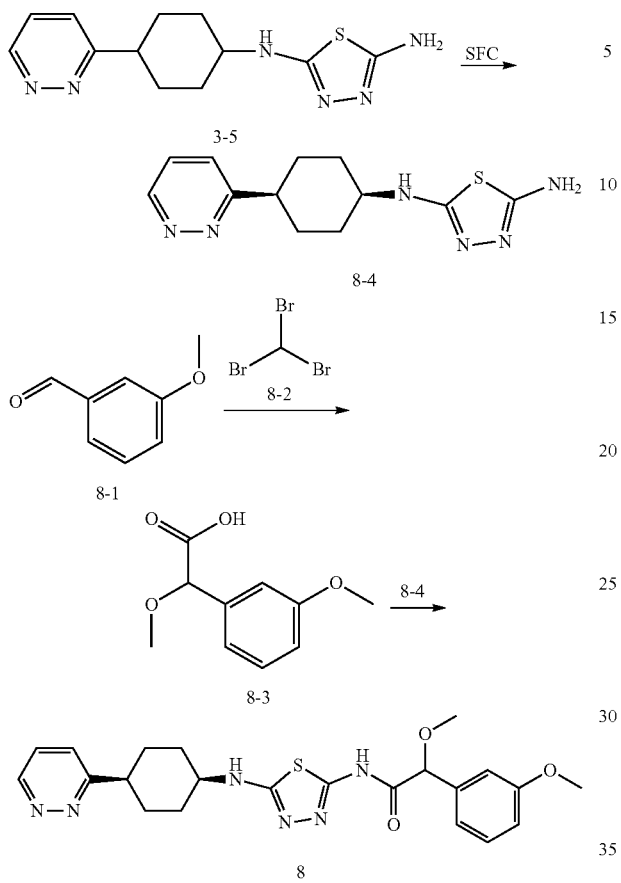

Step 1: Compound 3-5 was resolved by supercritical fluid chromatography (chromatographic column: DAICEL CHIRALPAK AS (250 mm*50 mm, 10 m; mobile phase: A: CO$_2$ B: ethanol (0.1% ammonia); gradient: 35%; flow rate: 100 mL/min; column temperature: 40° C.; elution time: 10.0 min) to obtain compound 8-4 with the retention time of 4.21 min. MS ESI calculated value for C$_{12}$H$_{16}$N$_6$S [M+H]$^+$ 277, measured value 277.

Step 2: Compound 8-1 (5 g, 36.72 mmol) and compound 8-2 (11.14 g, 44.07 mmol) were dissolved in methanol (50 mL), and a solution of potassium hydroxide (11.33 g, 201.99 mmol) in methanol (100 mL) was added dropwise thereto at 0° C. After completion of the dropwise addition, the reaction solution was stirred at 25° C. for 24 hours. The reaction solution was filtered, and the filtrate was evaporated to dryness. Water (300 mL) was added to the residue, and then the mixture was washed with methyl tert-butyl ether (300 mL). The aqueous phase was adjusted to pH=6 with 1 N hydrochloric acid to precipitate a solid, which was filtered and dried to obtain compound 8-3. $^1$HNMR (400 MHz, CDCl$_3$) δ ppm 3.39 (s, 3H), 3.79 (s, 3H), 4.74 (s, 1H), 6.89 (dd, J=8.16, 2.13 Hz, 1H), 6.95-7.04 (m, 2H), 7.24-7.31 (m, 1H), 9.88-10.16 (m, 1H).

Step 3: Compound 8-3 (21.30 mg, 108.55 μmol) and compound 8-4 (30.00 mg, 108.55 mol) were dissolved in DMF (5 mL), and then T3P (48.42 μL, 162.82 μmol, 50% solution in ethyl acetate) and DIEA (21.04 mg, 162.82 μmol) were added thereto. The reaction solution was stirred at 40° C. for 1 hour. After completion of the reaction, a sodium bicarbonate aqueous solution (5 mL) was added, and the solution was then extracted with ethyl acetate (20 mL*3). The organic phase was washed with saturated brine (10 mL), dried over anhydrous sodium sulfate, filtered and evaporated to remove the solvent. The residue was separated by preparative high performance liquid chromatography (chromatographic column: Boston Green ODS 150*30 mm, 5 m; mobile phase: water (0.1% TFA)-ACN; B (acetonitrile) %: 25%-47.5%, 7 min) to obtain the trifluoroacetate salt of compound 8. MS ESI calculated value for C$_{22}$H$_{26}$N$_6$O$_3$S [M+H]$^+$ 455, measured value 455. $^1$HNMR (400 MHz, MeOD) δ ppm 1.93-2.14 (m, 9H), 3.46 (s, 3H), 3.82 (s, 3H), 3.97-4.02 (m, 1H), 4.97 (s, 1H), 6.93-6.97 (m, 1H), 7.04-7.08 (m, 2H), 7.32 (t, J=8.03 Hz, 1H), 7.97-8.02 (m, 1H), 8.04-8.09 (m, 1H), 9.24 (d, J=4.02 Hz, 1H). The hydrochloride salt of compound 8 was subjected to post-processing to obtain compound 8.

The compounds shown in Table 1 can be prepared by a method similar to that for preparing compound 8, wherein Example 10 was prepared using commercial chiral carboxylic acid. The hydrochloride salt or trifluoroacetate salt of a compound was subjected to post-processing to obtain the compound:

TABLE 1

| Example | Structural formula | Separation method, LCMS and $^1$HNMR |
| --- | --- | --- |
| Compound 9 (hydrochloride salt) | | Chromatographic column: Agela DuraShell 150 mm_25 mm_5 μm; mobile phase: [water (0.05% HCl)-ACN]; B (acetonitrile)%: 26%-56%, 8.5 min; MS ESI calculated value for C$_{20}$H$_{23}$F$_3$N$_6$O$_3$S [M + H]$^+$ 509, measured value 509. $^1$HNMR (400 MHz, MeOD) δ ppm 1.93-2.21 (m, 9 H) 3.51 (s, 3 H) 4.05 (br s, 1 H) 5.11 (s, 1 H) 7.32 (br d, J = 6.78 Hz, 1 H) 7.45 (s, 1 H) 7.48-7.56 (m, 2 H) 8.55 (dd, J = 8.53, 5.27 Hz, 1 H) 8.73 (d, J = 8.53 Hz, 1 H) 9.53 (d, J = 5.02 Hz, 1 H) |

TABLE 1-continued

| Example | Structural formula | Separation method, LCMS and $^1$HNMR |
|---|---|---|
| Compound 10 (hydrochloride salt) | | Chromatographic column: Agela DuraShell 150 mm_25 mm_5 μm; mobile phase: [water (0.05% HCl)-ACN]; B (acetonitrile)%: 12%-42%, 11.3 min; MS ESI calculated value for $C_{20}H_{23}F_3N_6O_3S$ [M + H]$^+$ 425, measured value 425. $^1$HNMR (400 MHz, MeOD) δ ppm 1.93-2.25 (m, 9 H) 3.46 (s, 3 H) 4.06 (br s, 1 H) 5.01 (s, 1 H) 7.33-7.44 (m, 4 H) 7.46-7.52 (m, 2 H) 8.54 (br s, 1 H) 8.75 (br d, J = 6.78 Hz, 1 H) 9.53 (br s, 1 H) |
| Compound 11 (trifluoroacetate salt) | | Chromatographic column: Boston Green ODS 150*30 mm; 5 μm; mobile phase: [water (0.1% TFA)-ACN]; B (acetonitrile)%: 17%-47%, 8 min; MS ESI calculated value for $C_{20}H_{23}F_3N_6O_3S$ [M + H]$^+$ 491, measured value 491. $^1$HNMR (400 MHz, MeOD) δ ppm 1.93-2.21 (m, 9 H), 3.48 (s, 3 H), 4.01 (br s, 1 H), 5.03 (s, 1 H), 6.86 (t, J = 74.4 Hz, 1 H), 7.16 (dd, J = 7.60 Hz & 1.60 Hz, 1 H), 7.30 (s, 1 H), 7.31-7.43 (m, 2 H), 8.03-8.13 (m, 2 H), 9.26 (br s, 1 H) |
| Compound 12 (trifluoroacetate salt) | | Chromatographic column: Boston Green ODS 150*30 mm; 5 μm; mobile phase: [water (0.1% TFA)-ACN]; B (acetonitrile)%: 17%-47%, 8 min; MS ESI calculated value for $C_{20}H_{23}F_3N_6O_3S$ [M + H]$^+$ 473, measured value 473. $^1$HNMR (400 MHz, MeOD) δ ppm 1.85-2.25 (m, 9 H) 3.46 (s, 3 H), 3.90 (s, 3 H), 4.06 (brs, 1 H), 5.01 (s, 1 H), 7.05-7.25 (m, 3 H), 8.02 (d, J = 8.40 Hz, 1 H), 8.04-8.11 (m, 1 H), 9.25 (d, J = 4.40 Hz, 1 H). |

Example 13: Preparation of Compound 13 (Trifluoroacetate Salt)
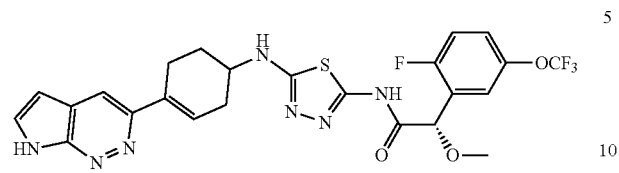
Synthetic Route:
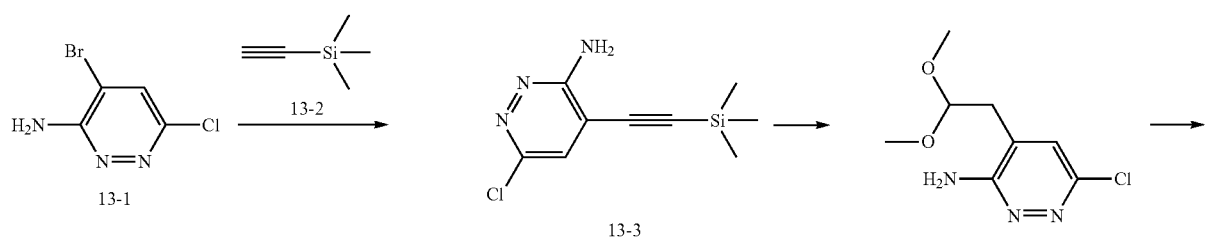
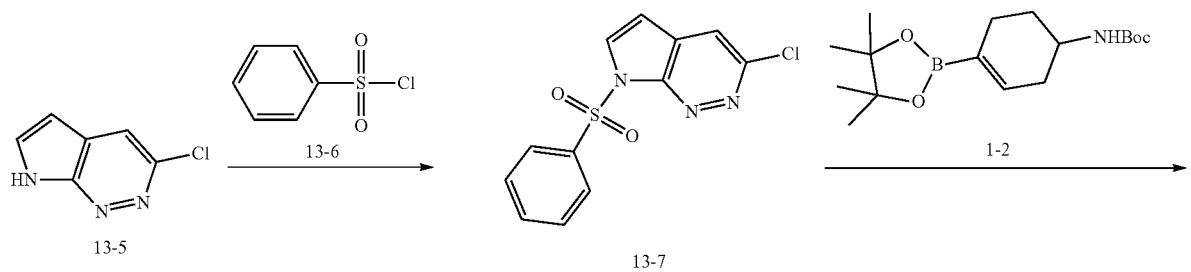
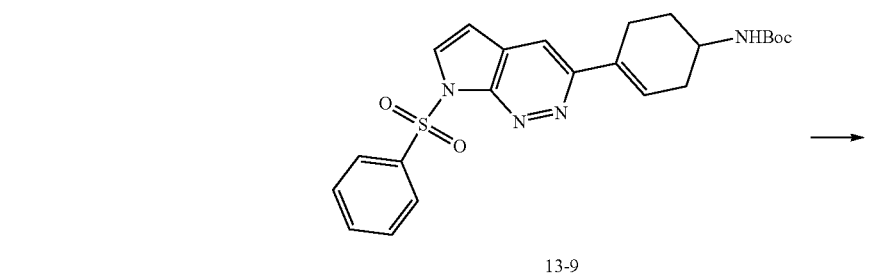
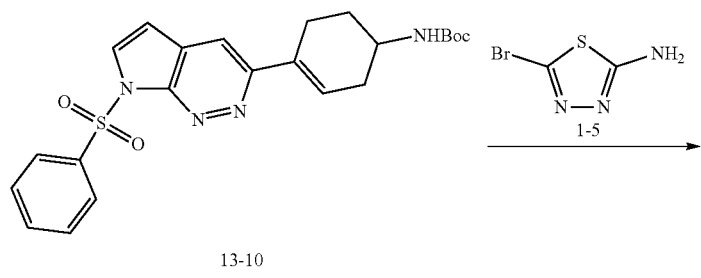

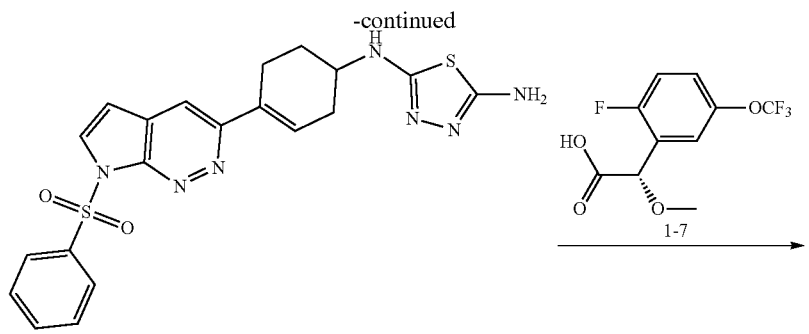

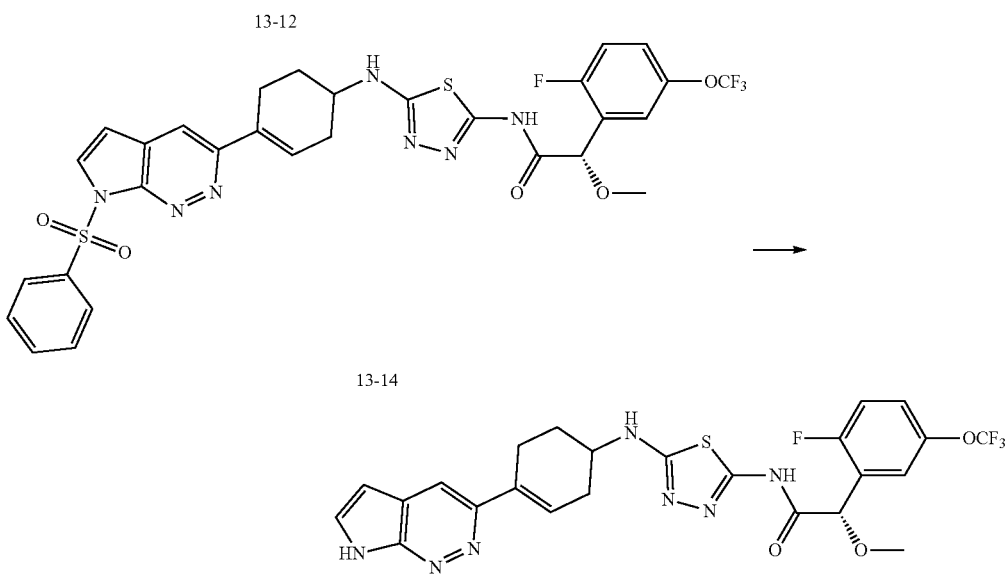

Step 1: Compound 13-1 (6.0 g, 28.78 mmol), compound 13-2 (3.11 g, 31.66 mmol), triethylamine (7.28 g, 71.96 mmol), cuprous iodide (548 mg, 2.88 mmol), and Pd(PPh$_3$)$_2$Cl$_2$ (2.02 g, 2.88 mmol) were added to toluene (200 mL), and the reaction solution was stirred at 25° C. for 12 hours under nitrogen protection. After completion of the reaction, water (50 mL) was added, and the reaction solution was extracted with ethyl acetate (50 mL*3) dried and concentrated. The residue was purified by column chromatography (petroleum ether/ethyl acetate=1:1) to obtain compound 13-3. MS ESI calculated value for C$_9$H$_{12}$ClN$_3$Si [M+H]$^+$ 226, measured value 226.

Step 2: To a solution of compound 13-3 (5.5 g, 24.36 mmol) in methanol (200 mL) was added potassium carbonate (540 mg, 3.91 mmol), and the reaction solution was stirred at 60° C. for 3 hours. The reaction solution was filtered and concentrated to obtain compound 13-4. MS ESI calculated value for C$_8$H$_{12}$ClN$_3$O$_2$ [M+H]$^+$ 218, measured value 218.

Step 3: To a solution of compound 13-4 (5.3 g, 24.35 mmol) in ethanol (100 mL) was added hydrochloric acid (35.33 mL, 1 N), and the reaction solution was stirred at 60° C. for 2 hours. The reaction solution was filtered and concentrated. The residue was purified by column chromatography (petroleum ether/ethyl acetate=1:1) to obtain compound 13-5. MS ESI calculated value for C$_6$H4ClN$_3$ [M+H]$^+$ 154, measured value 154.

Step 4: To a solution of compound 13-5 (0.5 g, 3.26 mmol) in acetonitrile (20 mL) were added compound 13-6 (690 mg, 3.91 mmol) and potassium carbonate (540 mg, 3.91 mmol), and the reaction solution was stirred at 25° C. for 2 hours. The reaction solution was filtered and concentrated. The residue was purified by column chromatography (petroleum ether/ethyl acetate=3:1) to obtain compound 13-7. MS ESI calculated value for C$_{12}$H$_8$ClN$_3$O$_2$S [M+H]$^+$ 294, measured value 294.

Step 5: To a solution of compound 13-7 (0.10 g, 0.34 mmol) in 1,4-dioxane (4 mL) and water (1 mL) were added compound 1-2 (0.11 mg, 0.34 mmol), potassium phosphate (144 mg, 0.68 mmol) and Pd(dppf)Cl$_2$ (25 mg, 0.034 mmol), and the reaction solution was stirred at 80° C. for 2 hours under nitrogen protection. The reaction solution was filtered and concentrated. The residue was purified by preparative thin layer chromatography sheet (petroleum ether/ethyl acetate=2:1) to obtain compound 13-9. MS ESI calculated value for C$_{23}$H$_{26}$N$_4$O$_4$S [M+H]$^+$ 455, measured value 455.

Step 6: Compound 13-9 (120.0 mg, 0.26 mmol) was added to TFA/DCM (10 mL, 1:1), and the mixture was stirred at 25° C. for 10 minutes. After completion of the reaction, the reaction solution was evaporated to remove the solvent to obtain compound 13-10, which was directly used in the next reaction. MS ESI calculated value for C$_{18}$H$_{18}$N$_4$O$_2$S [M+H]$^+$ 355, measured value 355.

Step 7: Compound 13-10 (0.1 g, 0.28 mmol) and compound 1-5 (50.7 mg, 0.28 mmol) were dissolved in DMF (2 mL), and DIEA (72.93 mg, 0.56 mmol) was added thereto. The reaction solution was stirred at 80° C. for 12 hours. The reaction solution was filtered and evaporated to dryness. The residue was purified by preparative thin layer chromatography sheet (DCM/MeOH=10:1) to obtain compound 13-12. MS ESI calculated value for $C_{20}H_{19}N_7O_2S_2$ [M+H]$^+$ 454, measured value 454.

Step 8: Compound 13-12 (0.1 g, 0.22 mmol) and compound 1-7 (59 mg, 0.22 mmol) were dissolved in DMF (2 mL), and T3P (168 mg, 0.26 mmol, 50% solution in ethyl acetate), and DIEA (34 mg, 0.26 mmol) were added thereto successively. The reaction solution was stirred at 25° C. for 2 hours. After completion of the reaction, the reaction solution was concentrated, and the residue was purified by preparative thin layer chromatography sheet (DCM/MeOH=10:1) to obtain compound 13-14. MS ESI calculated value for $C_{30}H_{25}F_4N_7O_5S_2$ [M+H]$^+$ 704, measured value 704.

Step 9: Compound 13-14 (80.0 mg, 0.113 mmol) and lithium hydroxide (5.4 mg, 0.22 mmol) were added to anhydrous methanol (5.00 mL), and the mixture was stirred at 60° C. for 2 hours. After completion of the reaction, the reaction solution was directly concentrated to obtain the crude product of compound 8, which was separated and purified by preparative high performance liquid chromatography (chromatographic column: Boston Green ODS 150*30 mm; 5 m; mobile phase: [water (0.1% TFA)-ACN]; B (acetonitrile) %: 25%-55%, 8 min) to obtain the trifluoroacetate salt of compound 13. MS ESI calculated value for $C_{24}H_{21}F_4N_7O_3S$ [M+H]$^+$ 564, measured value 564. $^1$H NMR (400 MHz, CDCl$_3$) δ ppm 1.93-2.26 (m, 2H), 2.36-2.91 (m, 4H), 3.42 (s, 3H), 3.67-3.86 (m, 1H), 5.16 (s, 1H), 6.31 (brs, 1H), 6.76 (d, J=3.26 Hz, 1H), 7.08-7.15 (m, 1H), 8.21 (s, 2H), 10.85 (brs, 1H), 13.37 (brs, 1H). The hydrochloride salt of compound 13 was subjected to post-processing to obtain compound 13.

Example 14: Compound 14

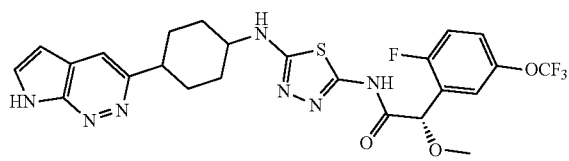 [SMILES: CO[C@H](C(=O)Nc1nnc(NC2CCC(c3cc4cc[nH]c4nn3)CC2)s1)c1cc(OC(F)(F)F)ccc1F]

Synthetic Route:

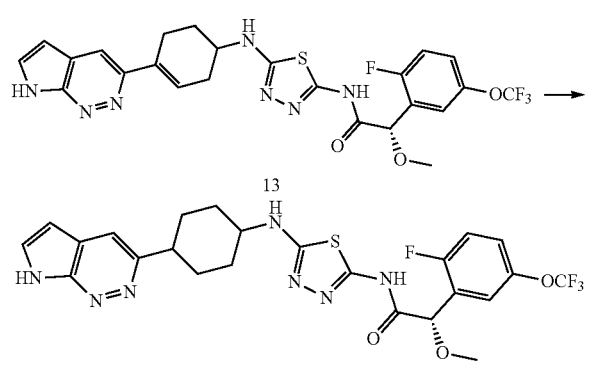

Step 1: Compound 13 (30.0 mg, 0.053 mmol) was added to methanol (3 mL), and then dry palladium on carbon (10% purity, 3 mg) was added thereto. The reaction solution was replaced with hydrogen three times and stirred at 25° C. for 1 hour under 15 psi hydrogen. The reaction solution was filtered and concentrated. The residue was purified by preparative thin layer chromatography sheet (DCM:MeOH=10:1) to obtain compound 14. MS ESI calculated value for $C_{24}H_{23}F_4N_7O_3S$ [M+H]$^+$ 566, measured value 566.

Experimental Example 1: Activity Test of Compounds in a GLS1 Coupling Reaction System Reagents and Instruments:

| Use | Name | Brand Catalog No |
|---|---|---|
| Buffer | Tris-HCl (pH 8.0) | Invitrogen-15568025 |
| | EDTA | Sigma E6758 |
| | K$_2$HPO$_4$ | Sigma-60353-250G |
| | BSA | Amresco-0332-100G |
| | DTT | Sigma-43815 |
| | Triton X-100 | Sigma-T9284-500 ml |
| Biochemical experiment | NAD+ | Sigma-N1636 |
| | L-glutamine | Sigma-49419 |
| | Glutamate Dehydrogenase (GIDH) | Roche-10197734001 |
| | GLS-1, His-tag | BPS (BPS Bioscience)-71102 |
| | Adenosine diphosphate | Sigma-01905-250MG-F |
| | DMSO | Sigma-D2650 |
| Experiment plate | Grenier Bio-one microclear 384 well | Grenier-781091 Grenier-781090 |
| ECHO compound plate | Labcyte Echo rated 384 well polypropylene plate | Labcyte-LP0200 Labcyte-LP05525 |
| Instrument | Labcyte ECHO 550 acoustic dispenser | Labcyte |
| | Multidrop Combi (Thermo) | Thermo |
| | Standard plastic tip dispensing cassette (Thermo) | Thermo-24072670 |
| | SpectraMax 340PC | / |

Preparations of Reagents:
Relevant reaction reagents should be prepared on the day of the experiment:
Preparation of 1× Assay Buffer
The final concentration of each component in the final experimental buffer was 50 mM Tris-HCl pH 8.0, 0.25 mM EDTA, 150 mM K$_2$HPO$_4$, 0.1 mg/mL BSA, 1 mM DTT, and 0.01% o Triton X-100.
Preparation of 2× Experimental Component Solution:
The reagent was taken out and put on ice to melt naturally for use;
the 1× assay buffer was used to prepare "solution A" in the experiment (solution A contained L-glutamine, NAD+ and GLDH), and the final concentration of each component in the final experimental reaction system was 4.5 mM L-glutamine, 2 mM NAD+, and 4 U/mL GLDH;
the 1× assay buffer was used to prepare "solution B" in the experiment—2× enzyme solution (solution B contained enzyme GLS1), and the final concentration of GLS1 in the final experimental reaction system was 2 nM.
Experiment Operation Steps:
The experiment plate was the plate prepared by Labcyte's ECHO that contained the gradient concentration of the compound and the corresponding DMSO solution before the experiment:
The experiment plate was taken out, and 20 μL of solution B (an enzyme GLS1 solution) was add to the 2$^{nd}$ to 23$^{rd}$ columns of the experiment plate, and then 20 μL of assay buffer was added to the 1st and 24th columns of the experiment plate, wherein the 1st and 24th columns were used as control groups of the experimental system;

the plate was centrifuged at 1000 rpm for 30 seconds;

the plate was sealed and incubated at 23° C. for 1 hour;

I after 1 hour incubation, 20 μL of solution A was added to columns 1 to 24 of the experiment plate (i.e., addition of samples to the whole plate);

the plate was centrifuged at 1000 rpm per second for 30 seconds;

the experiment plate was placed on SpectraMax 340PC, and read continuously for 20 minutes in the dynamic mode (the reading interval was set to 1 minute).

The inhibitory activity results of the compounds were shown in Table 2.

TABLE 2

Inhibitory activity results of the compounds on enzyme GLS1

| Compound No. | $IC_{50}$ (μM) for GLS1 |
|---|---|
| Compound 1 | 0.13159 |
| Compound 2 | 0.09653 |
| Compound 3 | 0.16959 |
| Compound 4 | 4.89696 |
| Compound 5 (hydrochloride salt) | 0.46890 |
| Compound 6 (hydrochloride salt) | 1.69324 |
| Compound 7 (hydrochloride salt) | 0.13320 |
| Compound 8 (trifluoroacetate salt) | 0.57678 |
| Compound 9 (hydrochloride salt) | 0.50163 |
| Compound 10 (hydrochloride salt) | 1.59079 |
| Compound 11 (trifluoroacetate salt) | 0.72024 |
| Compound 12 (trifluoroacetate salt) | 4.71123 |
| Compound 13 (trifluoroacetate salt) | 0.17976 |
| 14 | 0.75690 |

Experiment Conclusion:

The compounds designed in the present disclosure exhibit good GLS1 enzyme inhibitory activity, and have potential application value in the treatment of diseases related to cell proliferation.

Experimental Example 2: Pharmacokinetic Evaluation of Compounds

Objective: To test the in vivo pharmacokinetics of the compounds in mice

Experiment Materials:

C57BL/6 mice (female, 7-9 weeks old, Shanghai SLAC)

Experiment operations: The clear solution obtained by dissolving the test compound was administered to female C57BL/6 mice (overnight fasting, 7-9 weeks old) via tail intravenous injection and gavage, respectively. After administration of the test compound or the control compound, blood was collected from the mandibular vein of the intravenous injection group at 0.0833, 0.25, 0.5, 1, 2, 4, 6, 8 and 24 hours, and of the gavage group at 0.0833, 0.25, 0.5, 1, 2, 4, 6, 8 and 24 hours, respectively, and centrifuged to obtain plasma. The LC-MS/MS method was used to determine the blood drug concentration, and the WinNonlin™ Version 6.3 pharmacokinetic software was used to calculate the relevant pharmacokinetic parameters by the non-compartmental model linear logarithmic trapezoidal method. The test results were shown below:

TABLE 3

PK test results of the compounds in mice

| PK parameter | Compound 2 | CB-839 (control compound) |
|---|---|---|
| $T_{1/2}$ (hr) | 3.93 | 4.69 |
| $C_{max}$ (nM) | 36800 | 18105 |
| $AUC_{0-inf}$ (nM · hr) | 134054 | 27741 |
| Bioavailability (%) | 34.8 | 27.1 |

Note:
$T_{1/2}$: half-life;
$C_{max}$: Peak concentration;
$AUC_{0-inf}$: the area under the plasma concentration-time curve from time ero extrapolated to infinity;
Bioavailability: the extent to which the drug is bioavailable.

Note: $T_{1/2}$: half-life; $C_{max}$: Peak concentration; $AUC_{0-inf}$: the area under the plasma concentration-time curve from time zero extrapolated to infinity; Bioavailability: the extent to which the drug is bioavailable.

Conclusion: The compounds of the present disclosure have good oral bioavailability and higher exposure, which are beneficial to produce good in vivo efficacy.

Experimental Example 3 In Vivo Pharmacodynamic Study of a CB-17 SCID Nude Mouse Subcutaneous Xenograft Model of Human Myeloma RPMI-8226 Cell Objective: Pomalidomide is used to treat multiple myeloma, and this experiment is used to study and evaluate the in vivo efficacy of the test compound combined with pomalidomide in the CB-17 SCID nude mouse subcutaneous xenograft model of human myeloma RPMI-8226 cell.

Experiment animals: female CB-17 SCID nude mice, 6 to 8 weeks old, with the body weigh of 18 to 22 grams; Supplier: Shanghai Lingchang Biological Technology Co., Ltd.

Experiment Methods and Steps:

1.1 Cell Culture

Human myeloma RPMI 8226 cells were cultured in a monolayer in vitro. The culture conditions were: RPMI 1640 medium (brand: gibco—22400089, batch: 1894220) supplemented with 10% fetal bovine serum, 100 U/mL penicillin and 100 μg/mL streptomycin, at 37° C. and 5% $CO_2$. Conventional digestion treatment with pancreatin-EDTA for passage was carried out twice a week. When the cell confluence reached 80% to 90%, the cells were harvested, counted and inoculated.

1.2 Tumor Cell Inoculation (Tumor Inoculation)

0.2 mL ($6 \times 10^6$ cells) of RPMI 8226 cells (supplemented with matrigel in a volume ratio of 1:1) were subcutaneously inoculated on the right back of each mouse. The grouping and administration were started when the average tumor volume reached 374 mm³.

1.3 Preparation of the Test Substance

The test compound (compound 2) was formulated into a clear solution of 10 mg/mL, and the solvent was a 10 mM citric acid buffer containing 0.2% Tween-80 and 25% hydroxypropyl-β-cyclodextrin, pH=4. CB-839 was formulated into a clear solution of 10 mg/mL, and the solvent was a 10 mM citric acid buffer containing 25% hydroxypropyl-β-cyclodextrin, pH=2.2. Pomalidomide (Poma) was formulated into a clear solution of 0.1 mg/mL, and the solvent was 20% PEG400+80% (20% hydroxypropyl-β-cyclodextrin).

1.4 Tumor Measurement and Experimental Index

The experimental index was to investigate whether the tumor growth was inhibited, delayed or cured. Tumor diameter was measured twice a week with a vernier caliper. The calculation formula of tumor volume was $V=0.5 \times a \times b^2$, wherein a and b represented the long and short diameters of the tumor, respectively.

The anti-tumor efficacy of the compound was evaluated by TGI (%) or relative tumor proliferation rate T/C (%). TGI (%) reflected the tumor growth inhibition rate. Calculation of TGI (%): TGI (%)=[1−(average tumor volume at the end of administration in a treatment group−average tumor volume at the beginning of administration in this treatment group)/(average tumor volume at the end of administration in the solvent control group−average tumor volume at the beginning of administration in the solvent control group)]×100%.

Relative tumor proliferation rate T/C (%): the calculation formula was as follows: T/C %=$T_{RTV}/C_{RTV}$×100% ($T_{RTV}$: mean RTV of the treatment group; $C_{RTV}$: mean RTV of the negative control group). The relative tumor volume (RTV) was calculated according to the results of the tumor measurement. The calculation formula was RTV=$V_t/V_0$, where $V_0$ was the tumor volume measured at beginning of the grouping and administration (i.e., $d_0$), and $V_t$ was the tumor volume at the time of a certain measurement. $T_{RT}V$ and $C_{RTV}$ were obtained from the data on the same day.

1.5 Statistical Analysis

Statistical analysis included mean value and standard error (SEM) of the tumor volume of each group at each time point (see Table 4 for specific data). The treatment group showed the best treatment effect on day 14 after the administration at the end of the test, so the statistical analysis was performed based on this data to evaluate the differences between the groups. The comparison between two groups was analyzed by T-test, and the comparison between three or more groups was analyzed by one-way ANOVA. If the F value was significantly different, the Games-Howell test was applied. If the F value was not significantly different, the Dunnet (2-sided) test was used for analysis. All data analysis was performed with SPSS 17.0. $p<0.05$ was considered significantly different.

Statistical analysis of synergy: method for calculating Q value (also known as King's formula method) was as follows: Q=TGIA+B/(TGIA+TGIB−TGIA×TGIB). TGIA, TGIB and TGIA+B were the tumor inhibition rates when drug A was used alone, drug B was used alone, and drug A and drug B were used in combination, respectively.

1.6 Daily Observation of Experiment Animals

In the experiment, the effect of the test compound on the weight of the animal was investigated. At the same time, the animal's daily behavior and activities, food and water intake (visual inspection), physical signs or other abnormal conditions were routinely checked. The number of animal deaths and side effects in each group were recorded based on the number of animals in the group.

1.7 Test Results 1.7.1 Animal Weight

The weight of the experiment animals was used as a reference index for indirect determination of drug toxicity. In this model, none of the administration groups showed significant weight loss, morbidity or death. The effect of the test substance on the body weight in the female CB-17 SCID subcutaneously implanted tumor model of human myeloma RPMI-8226 cell was shown in FIG. 1.

1.7.2 Tumor Volume

The changes in tumor volume of each group after the administration of compound 2 in the female CB-17 SCID subcutaneously implanted tumor model of human myeloma RPMI-8226 cell were shown in Table 4.

TABLE 4

Evaluation of anti-tumor efficacy of compound 2 and CB-839 combined with pomalidomide (Poma) on a model of human myeloma RPMI-8226 transplantation tumor (calculated based on tumor volume on day 14 after administration)

| Groups | Tumor volume $(mm^3)^a$ (Day 14) | RTV (Day 14) | T/C[b] (%) | TGI[b] (%) | p value[c] |
|---|---|---|---|---|---|
| Blank (solvent control group), PO, BID | 2145 ± 308 | 6.13 ± 1.13 | — | — | — |
| Poma (1 mg/kg), PO, QD | 1542 ± 259 | 4.22 ± 0.50 | 68.8 | 34.0 | 0.465 |
| CB-839/Poma 100 mg/kg (D1-D10) 150 mg/kg (D11-D14)/ 1 mg/kg, PO, BID/QD | 1151 ± 264 | 2.89 ± 0.39 | 47.3 | 56.2 | 0.068 |
| Compound 2/Poma 100 mg/kg (D1-D10) 150 mg/kg (D11-D14)/ 1 mg/kg, PO, BID/QD | 1062 ± 166 | 2.83 ± 0.27 | 46.3 | 61.1 | 0.040 |

Note:

"—" no calculation;

PO: Oral administration;

BID: Twice a day;

QD: Once a day.

[a]Mean ± SEM.

[b]Tumor growth inhibition was calculated by T/C and TGI (TGI (%) = [1 − ($T_{21}$ − $T_0$)/($V_{21}$ − $V_0$)] × 100).

[c]The p value was calculated based on the tumor volume.

Note:
"--" no calculation; PO: Oral administration; BID: Twice a day; QD: Once a day.
a. Mean±SEM.
b. Tumor growth inhibition was calculated by T/C and TGI (TGI (%)=[1−($T_{21}$−$T_0$)/($V_{21}$−$V_0$)]×100).
c. The p value was calculated based on the tumor volume.

1.8 Test Conclusion and Discussion

In the model of human myeloma RPMI-8226 cell transplantation tumor, on day 14 after administration, the tumor volume of the tumor-bearing mice in the solvent control group reached 2,145 mm³, while the test substance pomalidomide (Poma), 1 mg/kg had no significant anti-tumor effect compared with the solvent control group (T/C=68.8%, TGI=34.0%, p=0.465) with the tumor volume of 1,542 mm³. Compared with the solvent control group, CB-839/Poma, 100/1 mg/kg had no significant anti-tumor effect (T/C=47.3%, TGI=56.2%, p=0.068) with the tumor volume of 1,151 mm³; compared with the solvent control group, compound 2/Poma 100/1 mg/kg had no significant anti-tumor effect (T/C=46.3%, TGI=61.1%, p=0.040) with the tumor volume of 1,062 mm³.

Using the Q value analysis method, the Q value of CB-839/Poma was less than 1.15, indicating that there was no synergy; using the Q value analysis method, the Q value of compound 2/Poma was greater than 1.15, indicating that there was a synergistic effect.

What is claimed is:

1. A compound of formula (I):

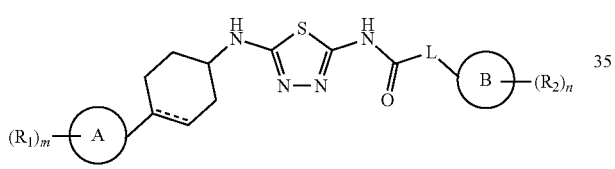

(I)

or a pharmaceutically acceptable salt or stereoisomer thereof,
wherein:
ring A is 5- to 10-membered heteroaryl, wherein the 5- to 10-membered heteroaryl contains 1, 2, 3, or 4 heteroatoms or heteroatomic groups independently selected from the group consisting of —N—, —NH—, —O—, and —S—;
ring B is phenyl or 5- or 6-membered heteroaryl, wherein the 5- or 6-membered heteroaryl contains 1, 2, 3, or 4 heteroatoms or heteroatomic groups independently selected from the group consisting of —N—, —NH—, —O—, and —S—;
L is —C($R_c$)($R_d$)—;
each $R_1$ is independently H, F, Cl, Br, I, CN, $C_{1-6}$ alkyl, $C_{1-6}$ heteroalkyl, C(O)OH, $NH_2$, or OH, wherein each $C_{1-6}$ heteroalkyl contains 1, 2, 3, or 4 heteroatoms or heteroatomic groups independently selected from the group consisting of —N—, —NH—, —O—, and —S—, and further wherein each $C_{1-6}$ alkyl and $C_{1-6}$ heteroalkyl is optionally and independently substituted with 1, 2, or 3 independently selected $R_a$ substituents;
each $R_2$ is independently H, F, Cl, Br, I, CN, $C_{1-6}$ alkyl, $C_{1-6}$ heteroalkyl, C(O)OH, $NH_2$, or OH, wherein each $C_{1-6}$ heteroalkyl contains 1, 2, 3, or 4 heteroatoms or heteroatomic groups independently selected from the group consisting of —N—, —NH—, —O—, and —S—, and further wherein each $C_{1-6}$ alkyl and $C_{1-6}$ heteroalkyl is optionally and independently substituted with 1, 2, or 3 independently selected $R_b$ substituents;
each $R_a$ is independently F, Cl, Br, I, CN, C(O)OH, $NH_2$, or OH;
each $R_b$ is independently F, Cl, Br, I, CN, C(O)OH, $NH_2$, or OH;
$R_c$ is H, F, Cl, Br, I, CN, $C_{1-6}$ alkyl, $C_{1-6}$ heteroalkyl, C(O)OH, $NH_2$, or OH, wherein the $C_{1-6}$ heteroalkyl contains 1, 2, 3, or 4 heteroatoms or heteroatomic groups independently selected from the group consisting of —N—, —NH—, —O—, and —S—, and further wherein the $C_{1-6}$ alkyl or $C_{1-6}$ heteroalkyl is optionally substituted with 1, 2, or 3 independently selected R substituents;
$R_d$ is H, F, Cl, Br, I, CN, $C_{1-6}$ alkyl, $C_{1-6}$ heteroalkyl, C(O)OH, $NH_2$, or OH, wherein the $C_{1-6}$ heteroalkyl contains 1, 2, 3, or 4 heteroatoms or heteroatomic groups independently selected from the group consisting of —N—, —NH—, —O—, and —S—, and further wherein the $C_{1-6}$ alkyl or $C_{1-6}$ heteroalkyl is optionally substituted with 1, 2, or 3 independently selected R substituents;
each R is independently F, Cl, Br, I, CN, $CH_3$, C(O)OH, $NH_2$, or OH;
m is 1, 2, or 3;
n is 1, 2, or 3; and ===== is a single bond or a double bond.

2. The compound as defined in claim 1, or a pharmaceutically acceptable salt or stereoisomer thereof, wherein ring A is pyridinyl, pyridazinyl, pyrazinyl, or 7H-pyrrolo[2,3-c]-pyridazinyl.

3. The compound as defined in claim 2, or a pharmaceutically acceptable salt or stereoisomer thereof, wherein

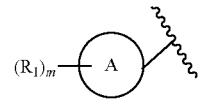

is:

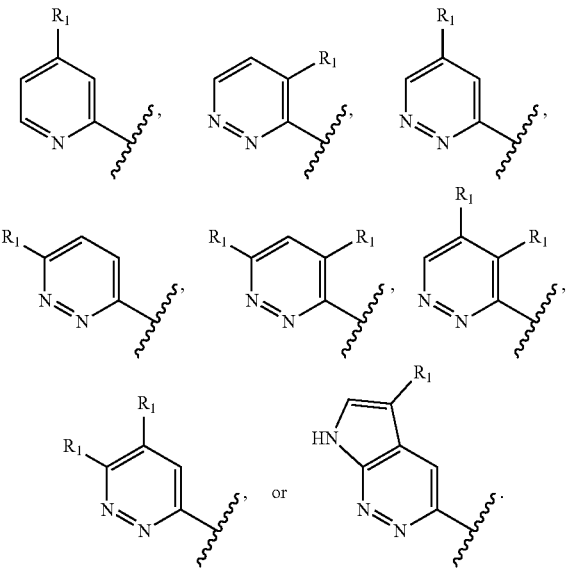

4. The compound as defined in claim 3, or a pharmaceutically acceptable salt or stereoisomer thereof, wherein

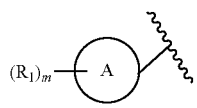

is:

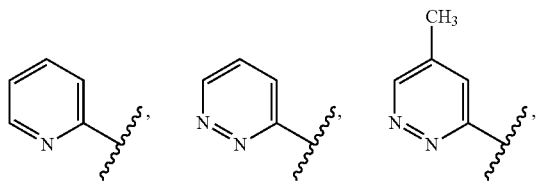

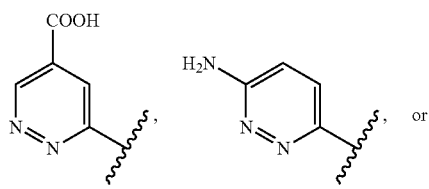

5. The compound as defined in claim 1, or a pharmaceutically acceptable salt or stereoisomer thereof, wherein ring B is phenyl, pyrazolyl, or pyridinyl.

6. The compound as defined in claim 5, or a pharmaceutically acceptable salt or stereoisomer thereof, wherein

is:

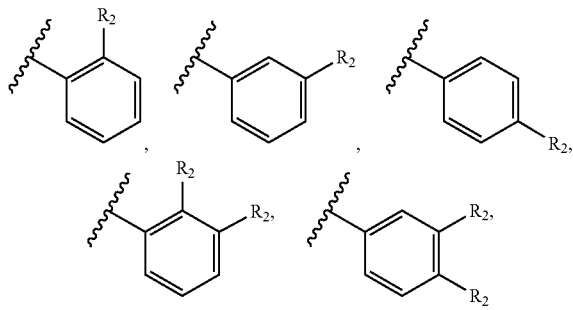

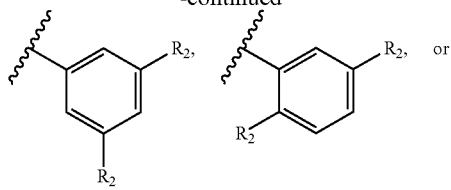

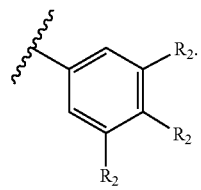

7. The compound as defined in claim 6, or a pharmaceutically acceptable salt or stereoisomer thereof, wherein

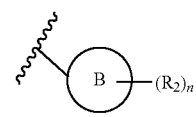

is:

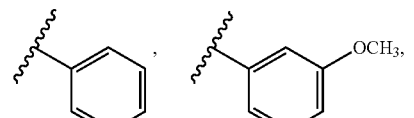

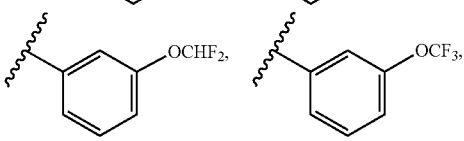

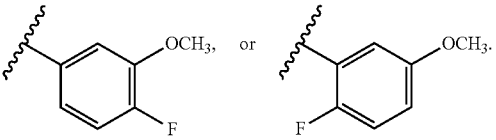

8. The compound as defined in claim 1, or a pharmaceutically acceptable salt or stereoisomer thereof, wherein L is —CH$_2$— or —CH(OCH$_3$)—.

9. The compound as defined in claim 8, or a pharmaceutically acceptable salt or stereoisomer thereof, wherein L is:

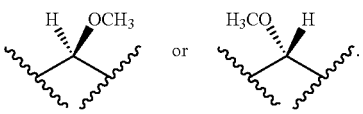

10. The compound as defined in claim 1, or a pharmaceutically acceptable salt or stereoisomer thereof, wherein each R$_1$ is independently H, F, Cl, Br, I, CN, C$_{1-3}$ alkyl, C(O)OH, NH$_2$, OH, or OC$_{1-3}$ alkyl, wherein each C$_{1-3}$ alkyl and OC$_{1-3}$ alkyl is optionally and independently substituted with 1, 2, or 3 independently selected R$_a$ substituents.

11. The compound as defined in claim 10, or a pharmaceutically acceptable salt or stereoisomer thereof, wherein each R$_1$ is independently H, F, Cl, Br, I, CN, CH$_3$, CH$_2$CH$_3$, C(O)OH, NH$_2$, OH, or OCH$_3$, wherein each CH$_3$, CH$_2$CH$_3$, and OCH$_3$ is optionally and independently substituted with 1, 2, or 3 independently selected R$_a$ substituents.

12. The compound as defined in claim 11, or a pharmaceutically acceptable salt or stereoisomer thereof, wherein each R$_1$ is independently H, F, Cl, Br, I, CN, CH$_3$, CH$_2$F, CHF$_2$, CF$_3$, CH$_2$CH$_3$, C(O)OH, NH$_2$, OH, OCH$_3$, OCHF$_2$, or OCF$_3$.

13. The compound as defined in claim 1, or a pharmaceutically acceptable salt or stereoisomer thereof, wherein each R$_2$ is independently H, F, Cl, Br, I, CN, C$_{1-3}$ alkyl, C(O)OH, NH$_2$, OH, or OC$_{1-3}$ alkyl, wherein each C$_{1-3}$ alkyl and OC$_{1-3}$ alkyl is optionally and independently substituted with 1, 2, or 3 independently selected R$_b$ substituents.

14. The compound as defined in claim 13, or a pharmaceutically acceptable salt or stereoisomer thereof, wherein each R$_2$ is independently H, F, Cl, Br, I, CN, CH$_3$, CH$_2$CH$_3$, C(O)OH, NH$_2$, OH, or OCH$_3$, wherein each CH$_3$, CH$_2$CH$_3$, and OCH$_3$ is optionally and independently substituted with 1, 2, or 3 independently selected R$_b$ substituents.

15. The compound as defined in claim 14, or a pharmaceutically acceptable salt or stereoisomer thereof, wherein each R$_2$ is independently H, F, Cl, Br, I, CN, CH$_3$, CH$_2$F, CHF$_2$, CF$_3$, CH$_2$CH$_3$, C(O)OH, NH$_2$, OH, OCH$_3$, OCHF$_2$, or OCF$_3$.

16. The compound as defined in claim 1, or a pharmaceutically acceptable salt or stereoisomer thereof, wherein:
R$_c$ is H, F, Cl, Br, I, CN, C$_{1-3}$ alkyl, C(O)OH, NH$_2$, OH, or OC$_{1-3}$ alkyl, wherein the C$_{1-3}$ alkyl or OC$_{1-3}$ alkyl is optionally substituted with 1, 2, or 3 independently selected R substituents; and
R$_d$ is H, F, Cl, Br, I, CN, C$_{1-3}$ alkyl, C(O)OH, NH$_2$, OH, or OC$_{1-3}$ alkyl, wherein the C$_{1-3}$ alkyl or OC$_{1-3}$ alkyl is optionally substituted with 1, 2, or 3 independently selected R substituents.

17. The compound as defined in claim 16, or a pharmaceutically acceptable salt or stereoisomer thereof, wherein:
R$_c$ is H, F, Cl, Br, I, CN, CH$_3$, CF$_3$, CH$_2$CH$_3$, C(O)OH, NH$_2$, OH, or OCH$_3$; and
R$_d$ is H, F, Cl, Br, I, CN, CH$_3$, CF$_3$, CH$_2$CH$_3$, C(O)OH, NH$_2$, OH, or OCH$_3$.

18. The compound as defined in claim 1, wherein the compound is of formula (I-1), formula (I-2), formula (I-3), formula (I-4), formula (I-5), formula (I-6), formula (I-7), or formula (I-8):

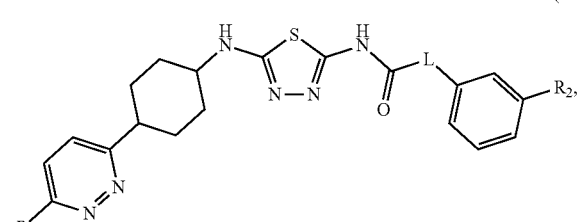

(I-1)

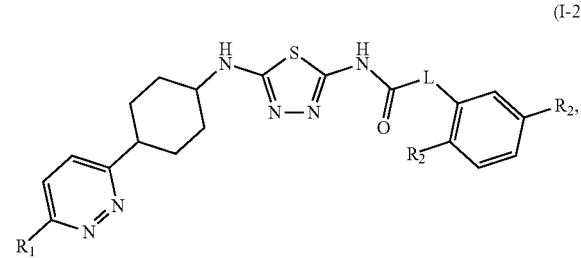

(I-2)

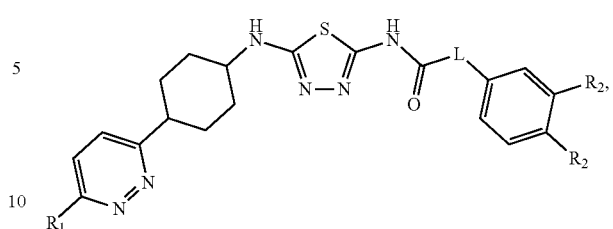

(I-3)

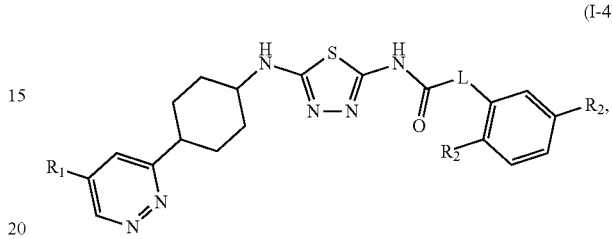

(I-4)

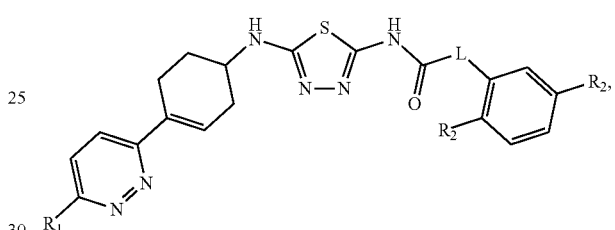

(I-5)

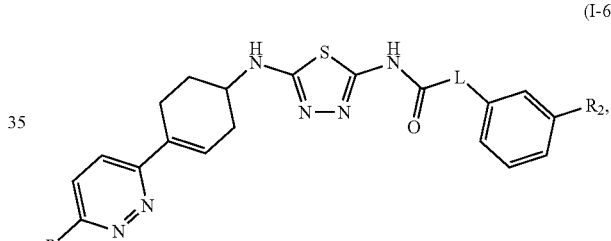

(I-6)

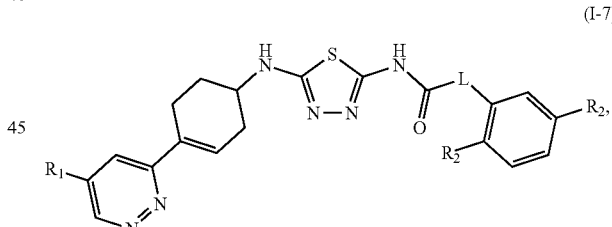

(I-7)

or

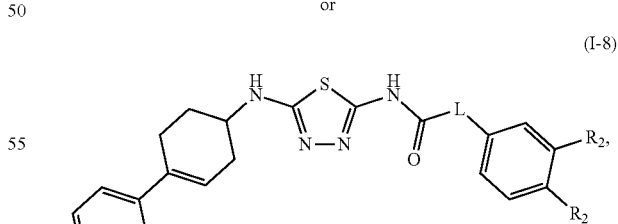

(I-8)

or a pharmaceutically acceptable salt or stereoisomer thereof.

19. The compound as defined in claim 18, or a stereoisomer thereof, wherein the stereoisomer of the compound is of formula (I-1a), formula (I-1b), formula (I-2a), formula (I-2b), formula (I-3a), formula (I-3b), formula (I-4a), formula (I-4b), formula (I-5a), or formula (I-5b):
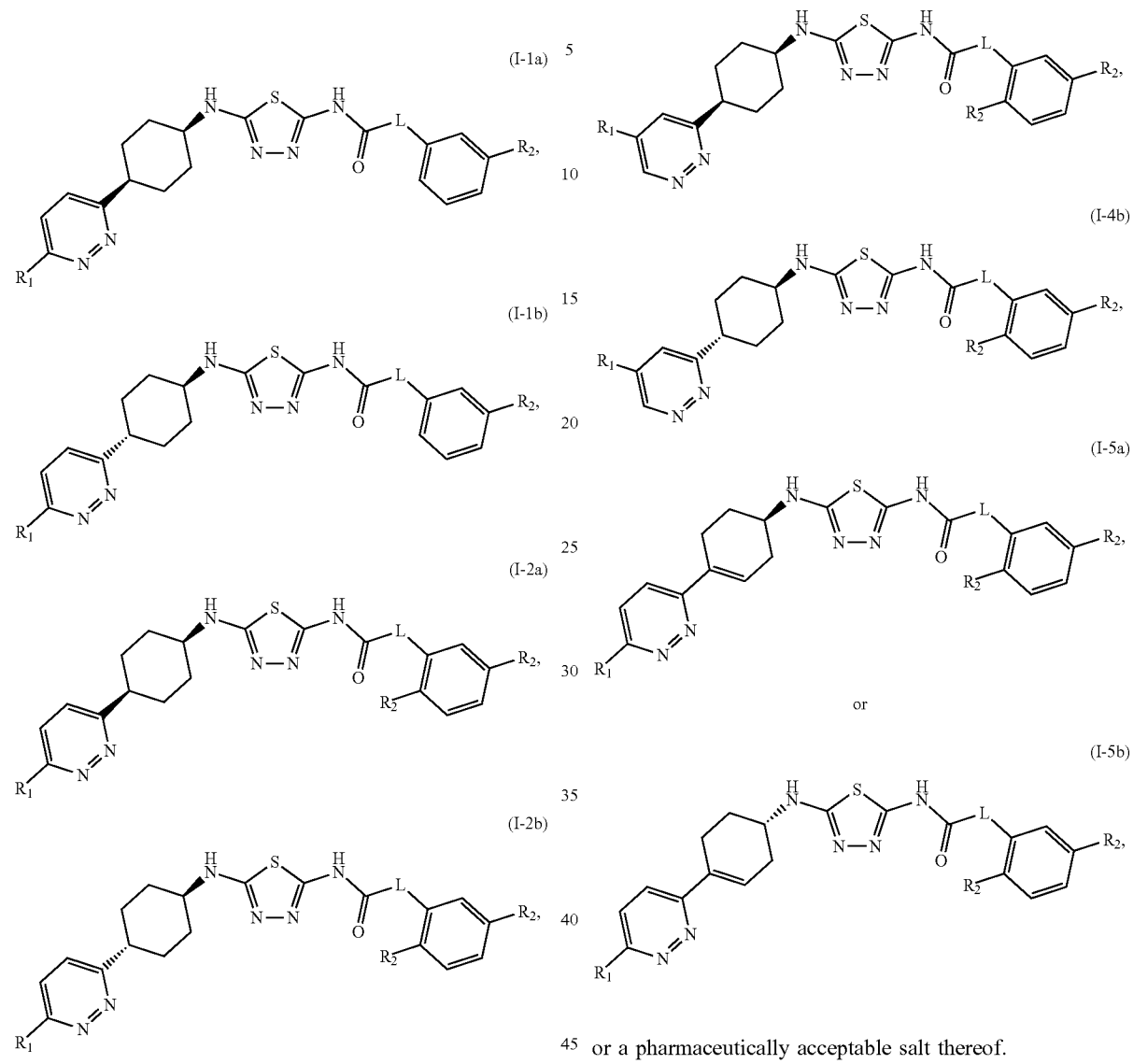
or a pharmaceutically acceptable salt thereof.
20. A compound selected from the group consisting of:
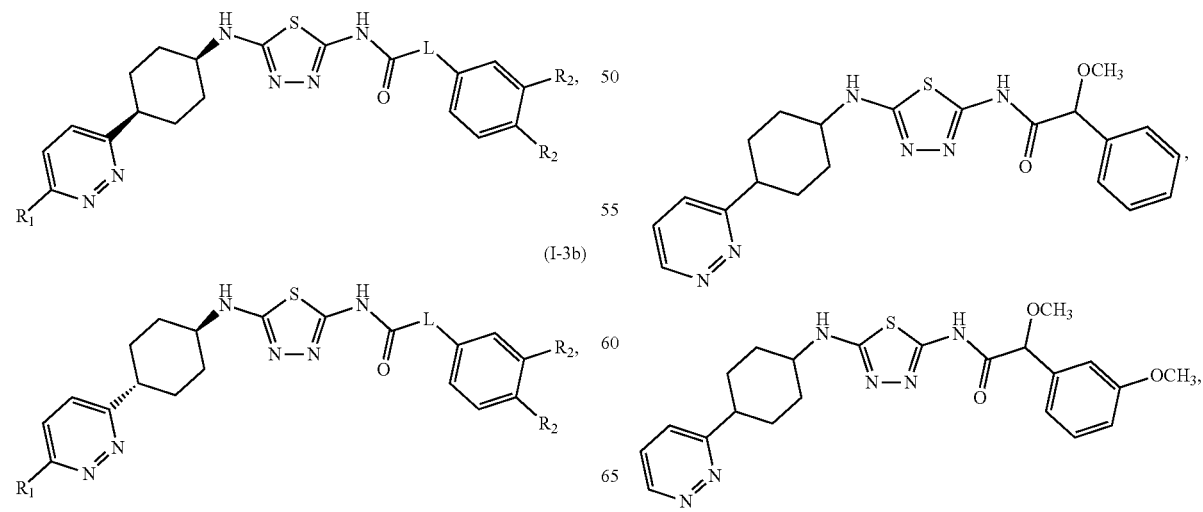

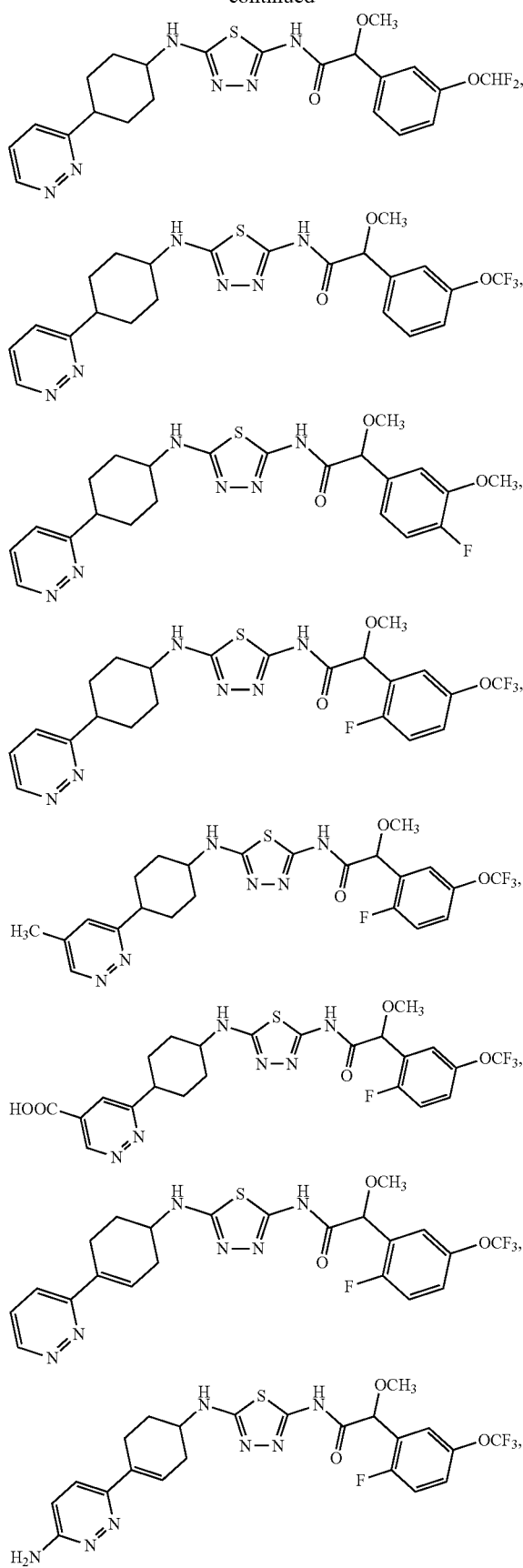
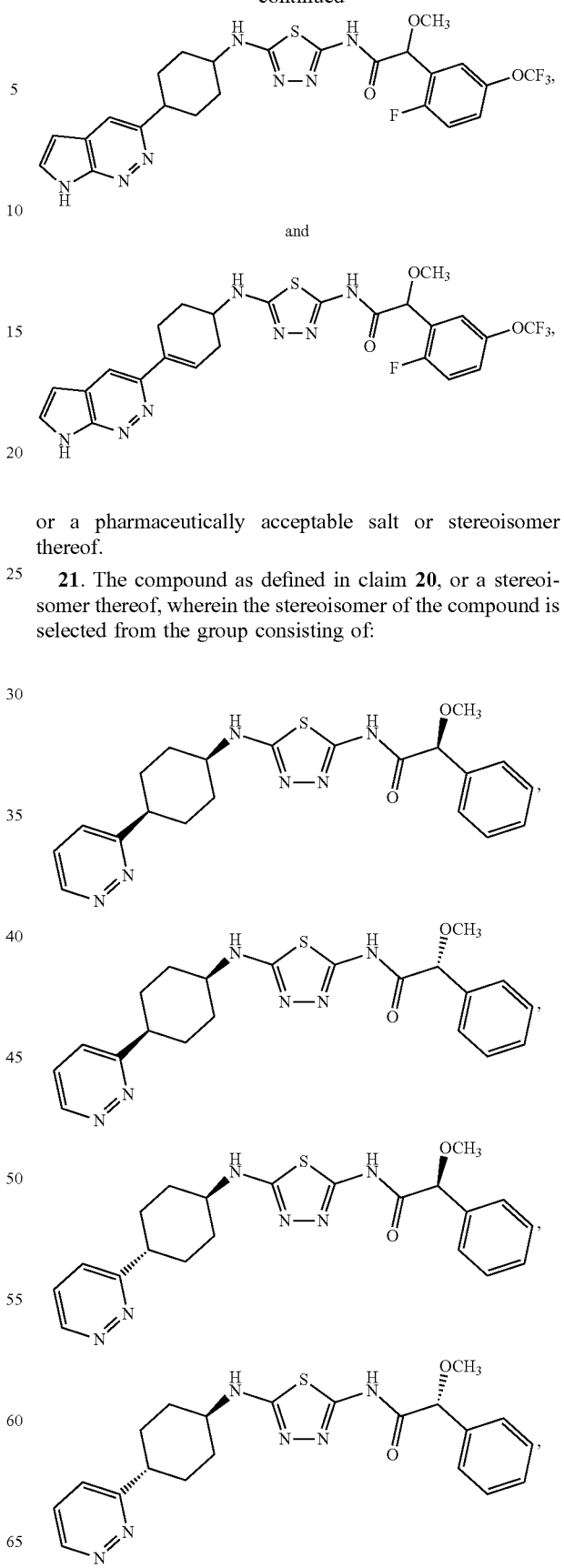
or a pharmaceutically acceptable salt or stereoisomer thereof.
21. The compound as defined in claim 20, or a stereoisomer thereof, wherein the stereoisomer of the compound is selected from the group consisting of:

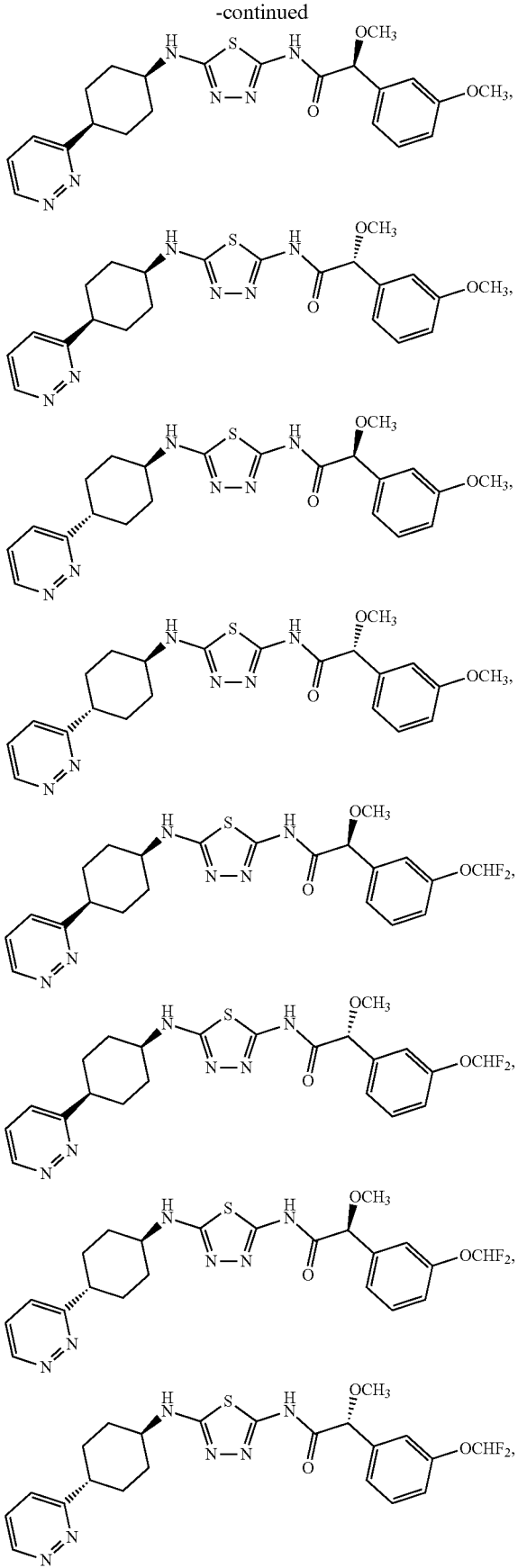
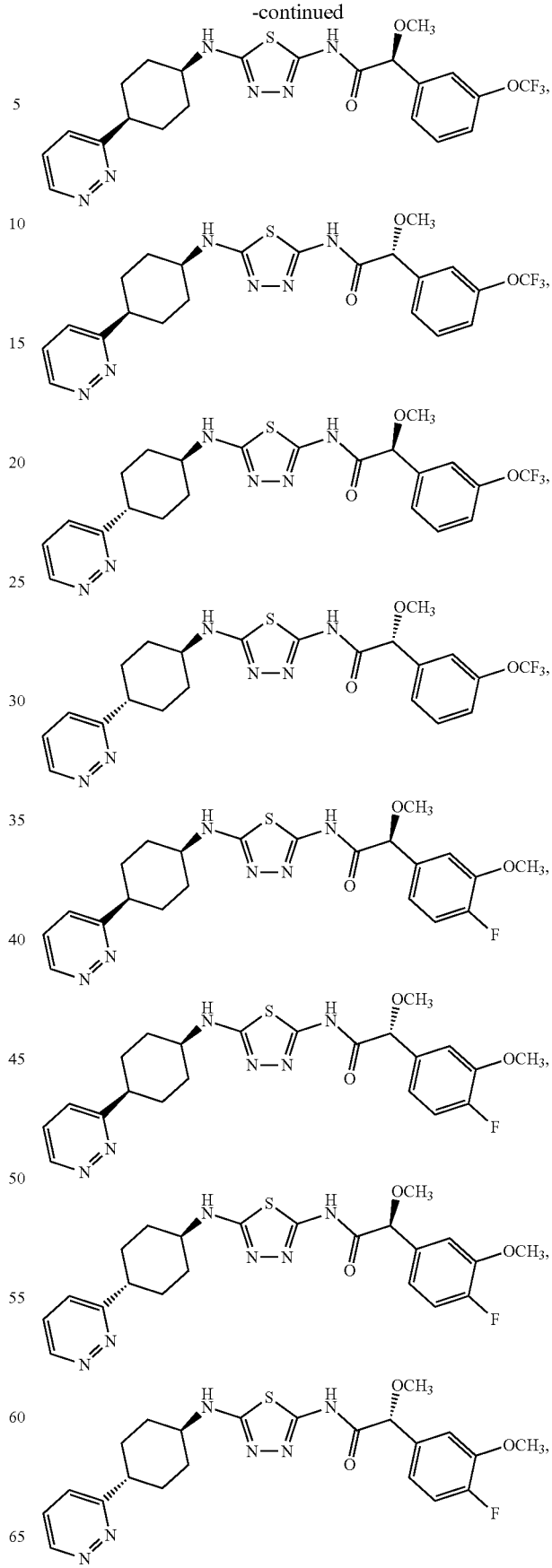

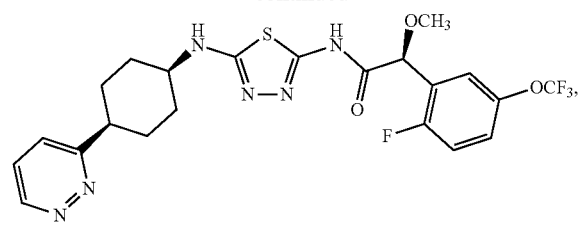
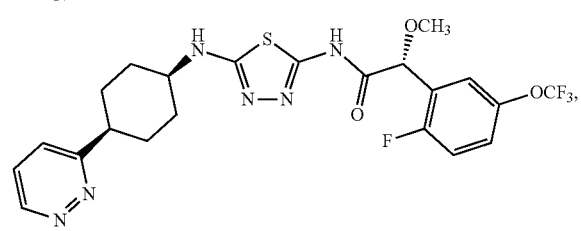
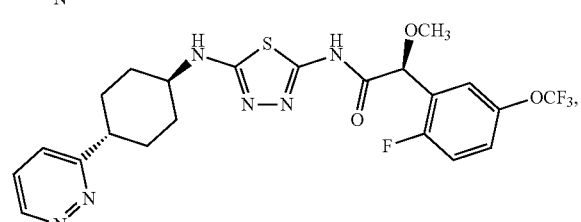
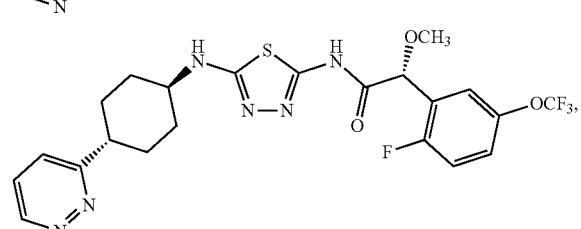
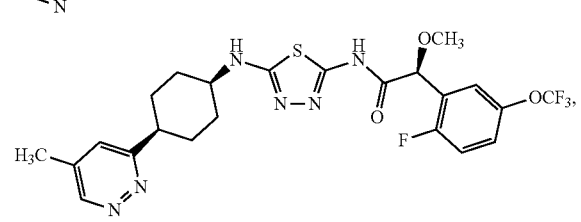
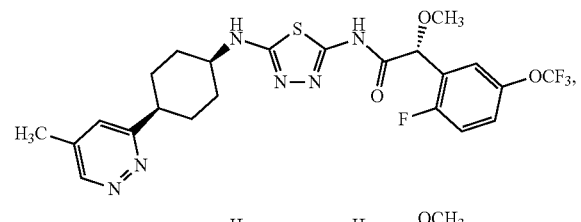
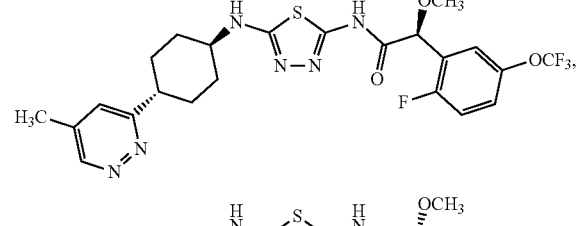
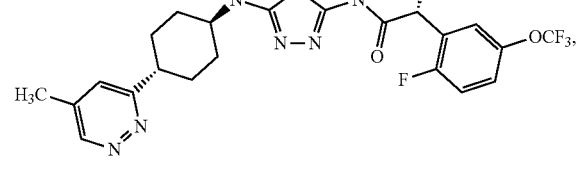
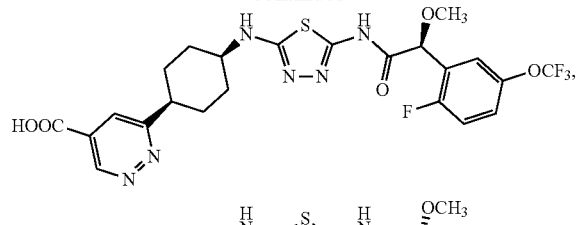
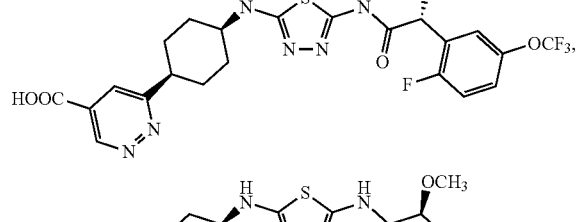
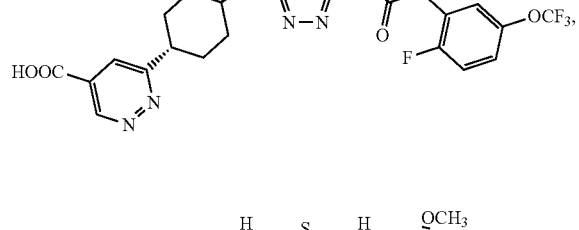
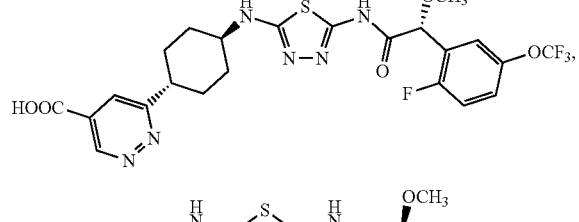
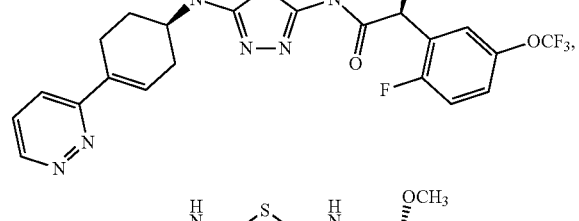
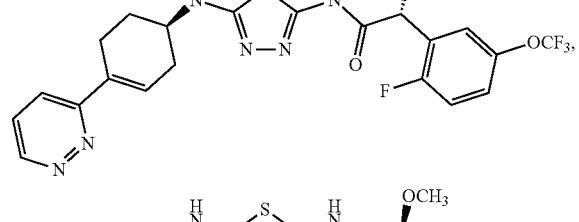
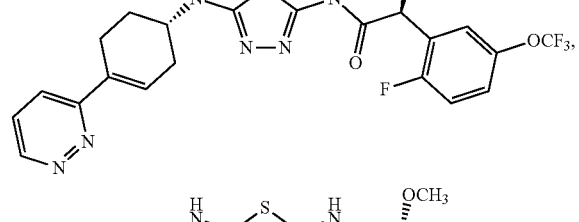
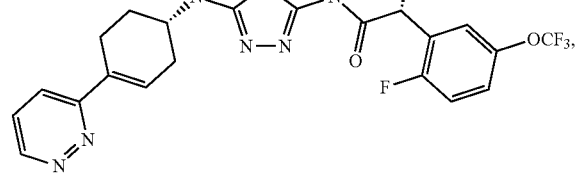

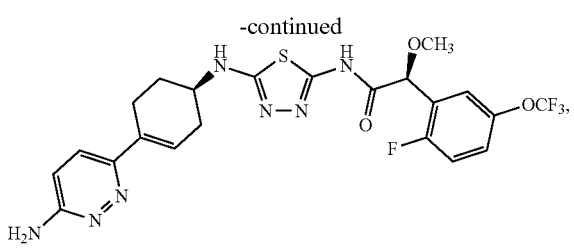
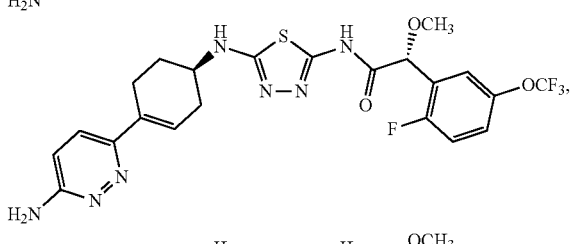
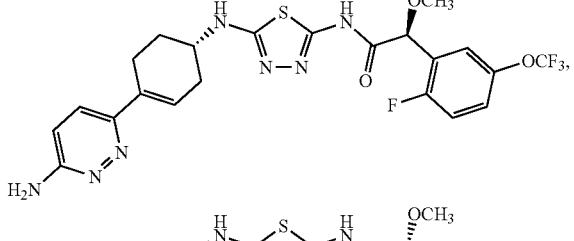
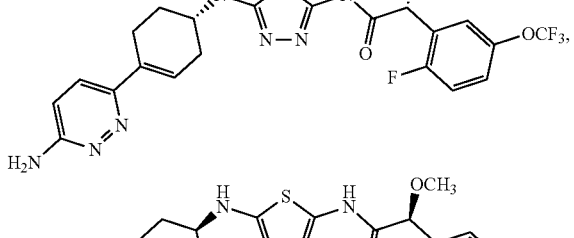
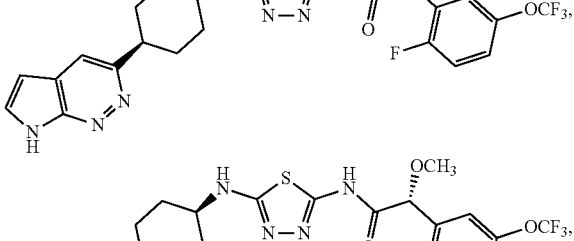
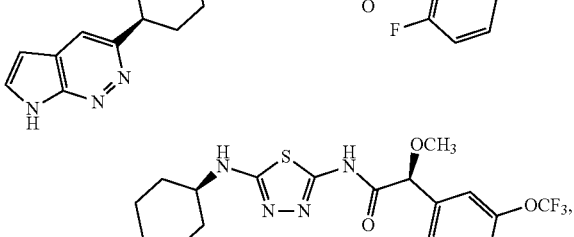
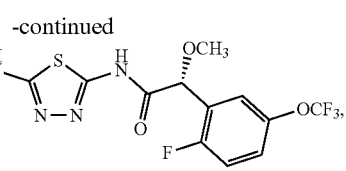
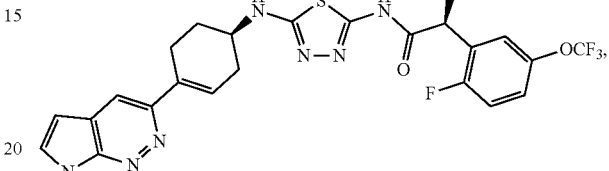
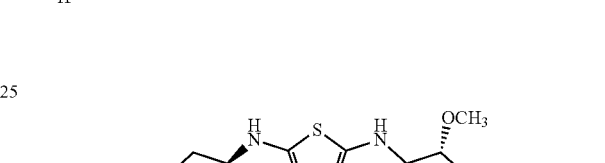
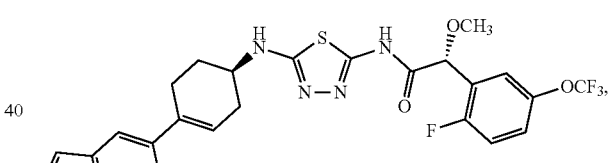
and
or a pharmaceutically acceptable salt thereof.
* * * * *